US012625152B2

(12) United States Patent
Matsushita et al.

(10) Patent No.: US 12,625,152 B2
(45) Date of Patent: May 12, 2026

(54) AUTOMATED SAMPLE ANALYZER

(71) Applicant: Beckman Coulter, Inc., Brea, CA (US)

(72) Inventors: Atsushi Matsushita, Shizuoka Prefecture (JP); Kevin L. Nowak, Waconia, MN (US); Takayuki Mizutani, Chaska, MN (US); Aaron P. O'Reilly, Chaska, MN (US)

(73) Assignee: Beckman Coulter, Inc., Brea, CA (US)

( * ) Notice: Subject to any disclaimer, the term of this patent is extended or adjusted under 35 U.S.C. 154(b) by 502 days.

(21) Appl. No.: 18/259,941

(22) PCT Filed: Dec. 22, 2021

(86) PCT No.: PCT/US2021/064952
§ 371 (c)(1),
(2) Date: Jun. 29, 2023

(87) PCT Pub. No.: WO2022/146842
PCT Pub. Date: Jul. 7, 2022

(65) Prior Publication Data
US 2024/0069047 A1 Feb. 29, 2024

Related U.S. Application Data

(60) Provisional application No. 63/131,458, filed on Dec. 29, 2020.

(51) Int. Cl.
*G01N 35/00* (2006.01)
*G16H 10/40* (2018.01)
*G16H 40/63* (2018.01)

(52) U.S. Cl.
CPC ....... *G01N 35/00722* (2013.01); *G16H 10/40* (2018.01); *G16H 40/63* (2018.01);
(Continued)

(58) Field of Classification Search
None
See application file for complete search history.

(56) References Cited

U.S. PATENT DOCUMENTS 10,372,468 B2 * 8/2019 Heo ........................ G06F 9/451
10,452,035 B2 * 10/2019 Goemann-Thoss ..... H04L 67/10
(Continued)

FOREIGN PATENT DOCUMENTS

WO WO-2022146842 A1 7/2022

OTHER PUBLICATIONS

"International Application Serial No. PCT/US2021/064952, International Search Report mailed May 31, 2022", 7 pgs.
(Continued)

*Primary Examiner* — Brian R Gordon
(74) *Attorney, Agent, or Firm* — Taft, Stettinius & Hollister LLP

(57) ABSTRACT

A system includes a sample analyzing device reading measurements associated with a liquid sample; a display device displaying a graphical user interface (GUI) to a current user of the automated sample analyzer; processing circuitry; and a memory storing: a receiving engine which receives the measurements associated with the liquid sample from the sample analyzing device and storing the received measurements in memory; a configuration control engine which sets a configuration of a user model to correspond to the current user of the automated sample analyzer; a learning engine which detects and collect at least one pattern of interaction of the current user with the GUI; and a user interface engine which configures the GUI according to user-dependent configuration data of the configuration of the user model corresponding to the current user.

20 Claims, 16 Drawing Sheets

(52) U.S. Cl.
CPC .............. *G01N 2035/00891* (2013.01); *G01N 2035/0097* (2013.01)

(56) References Cited

U.S. PATENT DOCUMENTS

| | | | | |
|---|---|---|---|---|
| 10,823,746 | B1 * | 11/2020 | Busa | G01N 33/56983 |
| 12,009,087 | B2 * | 6/2024 | Wu | G16H 70/40 |
| 2007/0233303 | A1 * | 10/2007 | Naito | G16H 40/40 |
| | | | | 700/108 |
| 2009/0259408 | A1 * | 10/2009 | Mishima | G01N 35/00722 |
| | | | | 702/19 |
| 2013/0139616 | A1 * | 6/2013 | Yamamoto | G16H 40/40 |
| | | | | 73/863.01 |
| 2015/0105877 | A1 * | 4/2015 | Goemann-Thoss | H04L 67/10 |
| | | | | 700/83 |
| 2016/0187360 | A1 * | 6/2016 | Shikata | G01N 35/00584 |
| | | | | 422/549 |
| 2018/0204111 | A1 * | 7/2018 | Zadeh | G06N 3/0464 |
| 2018/0315489 | A1 * | 11/2018 | Jaruzel | G16H 50/70 |
| 2019/0039034 | A1 * | 2/2019 | Siow | B01F 31/27 |
| 2019/0325330 | A1 * | 10/2019 | Roy | G06F 40/131 |
| 2020/0057880 | A1 | 2/2020 | Mizutani et al. | |
| 2020/0258633 | A1 | 8/2020 | Webb et al. | |
| 2020/0389470 | A1 * | 12/2020 | Kursun | G06N 3/08 |
| 2021/0071242 | A1 * | 3/2021 | Tidd | B01L 7/52 |
| 2022/0308895 | A1 * | 9/2022 | Ben-Elazar | G06N 3/045 |
| 2023/0045713 | A1 * | 2/2023 | Wohlstadter | G06F 3/0482 |
| 2023/0055848 | A1 * | 2/2023 | Kim | H04L 67/306 |
| 2023/0113064 | A1 * | 4/2023 | Yuk | G16H 50/20 |
| | | | | 700/90 |
| 2023/0132428 | A1 * | 5/2023 | Muse | A61B 5/091 |
| | | | | 128/204.23 |
| 2023/0290462 | A1 * | 9/2023 | Scott | G16H 15/00 |
| 2023/0325690 | A1 * | 10/2023 | Sathaye | G06N 3/045 |
| | | | | 706/12 |
| 2023/0352159 | A1 * | 11/2023 | Jensen | G01N 35/00722 |
| 2024/0055113 | A1 * | 2/2024 | Hansen | G16H 40/40 |

OTHER PUBLICATIONS

"International Application Serial No. PCT/US2021/064952, Invitation to Pay Additional Fees mailed Apr. 7, 2022", 11 pgs.
"International Application Serial No. PCT/US2021/064952, Written Opinion mailed May 31, 2022", 10 pgs.
Jain, Rahul, et al., "Contextual adaptive user interface for Android devices", 2013 Annual IEEE India Conference (Indicon), (Dec. 1, 2013), 1-5.

* cited by examiner

TRAINING PROCESS

FEATURE EXTRACTION LAYERS

CLASSIFIER

MAX POOLING

STRIDE OF 4

LEARN THE CLASSIFIER LAYER

700

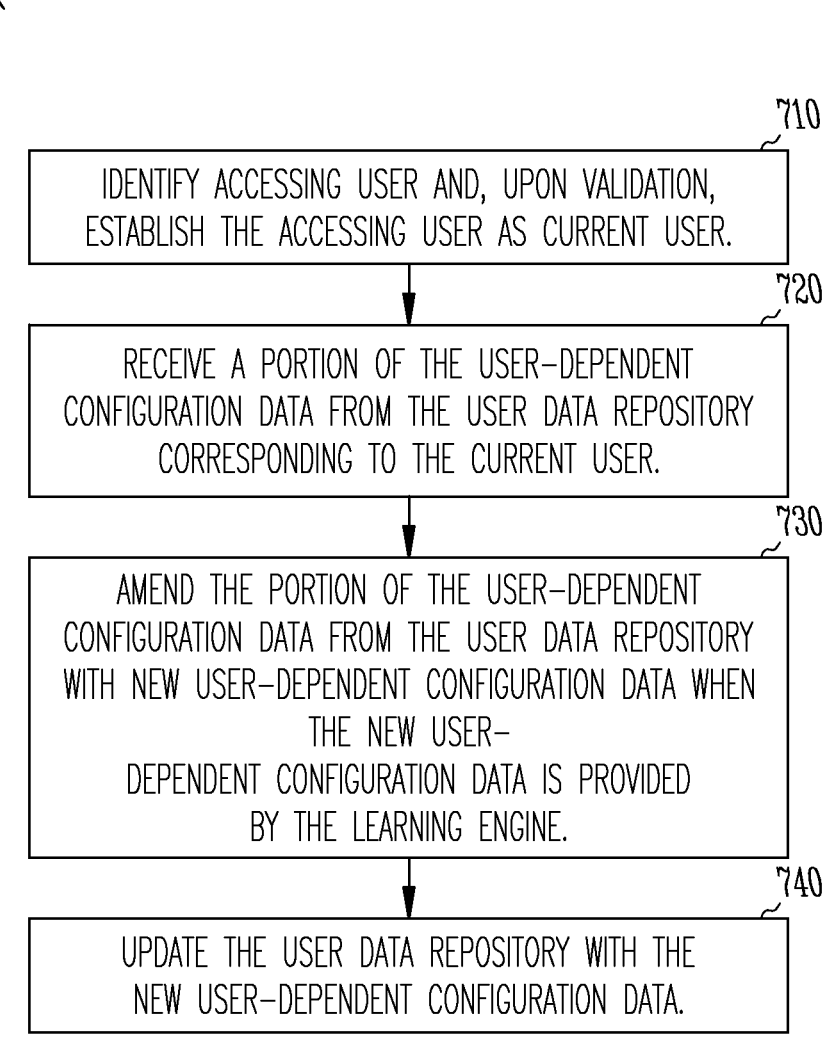

710

IDENTIFY ACCESSING USER AND, UPON VALIDATION, ESTABLISH THE ACCESSING USER AS CURRENT USER.

720

RECEIVE A PORTION OF THE USER-DEPENDENT CONFIGURATION DATA FROM THE USER DATA REPOSITORY CORRESPONDING TO THE CURRENT USER.

730

AMEND THE PORTION OF THE USER-DEPENDENT CONFIGURATION DATA FROM THE USER DATA REPOSITORY WITH NEW USER-DEPENDENT CONFIGURATION DATA WHEN THE NEW USER-DEPENDENT CONFIGURATION DATA IS PROVIDED BY THE LEARNING ENGINE.

740

UPDATE THE USER DATA REPOSITORY WITH THE NEW USER-DEPENDENT CONFIGURATION DATA.

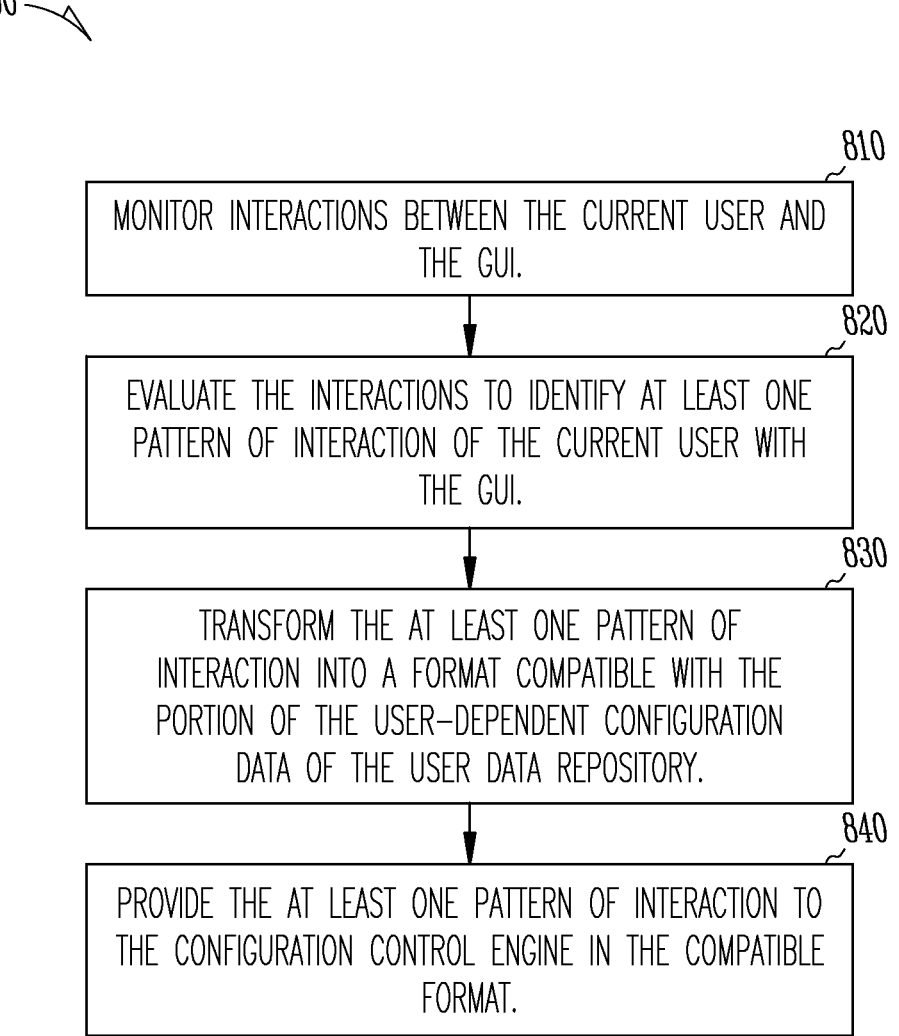

810

MONITOR INTERACTIONS BETWEEN THE CURRENT USER AND THE GUI.

820

EVALUATE THE INTERACTIONS TO IDENTIFY AT LEAST ONE PATTERN OF INTERACTION OF THE CURRENT USER WITH THE GUI.

830

TRANSFORM THE AT LEAST ONE PATTERN OF INTERACTION INTO A FORMAT COMPATIBLE WITH THE PORTION OF THE USER-DEPENDENT CONFIGURATION DATA OF THE USER DATA REPOSITORY.

840

PROVIDE THE AT LEAST ONE PATTERN OF INTERACTION TO THE CONFIGURATION CONTROL ENGINE IN THE COMPATIBLE FORMAT.

Fig. 8

AUTOMATED SAMPLE ANALYZER

PRIORITY CLAIM AND CROSS-REFERENCE TO RELATED APPLICATION

This application is a U.S. national stage filing under 35 U.S.C. § 371 from International Application No. PCT/US2021/064952, filed on Dec. 22, 2021, and published as WO 2022/146842 on Jul. 7 2022, which claims priority to U.S. Provisional Application Ser. No. 63/131,458 filed Dec. 29, 2020, the benefit of priority of each of which is claimed herein, and which applications and publication are hereby incorporated by reference herein in its their entirety.

TECHNICAL FIELD

Implementations pertain to an automated sample analyzer for analyzing liquid samples.

BACKGROUND

Automated sample analyzers for analyzing liquid samples are, oftentimes, used by many different people (e.g., scientific researchers, lab technicians, repair persons, and the like) with different use cases. However, the automated sample analyzer may provide the same user interface for each and every user.

BRIEF DESCRIPTION OF THE DRAWINGS

FIG. 7 is a flow chart illustrating an example method for updating a user data repository, in accordance with some implementations.

FIG. 8 is a flow chart illustrating an example method for identifying and storing a pattern of interaction, in accordance with some implementations.

SUMMARY

Figure 1:
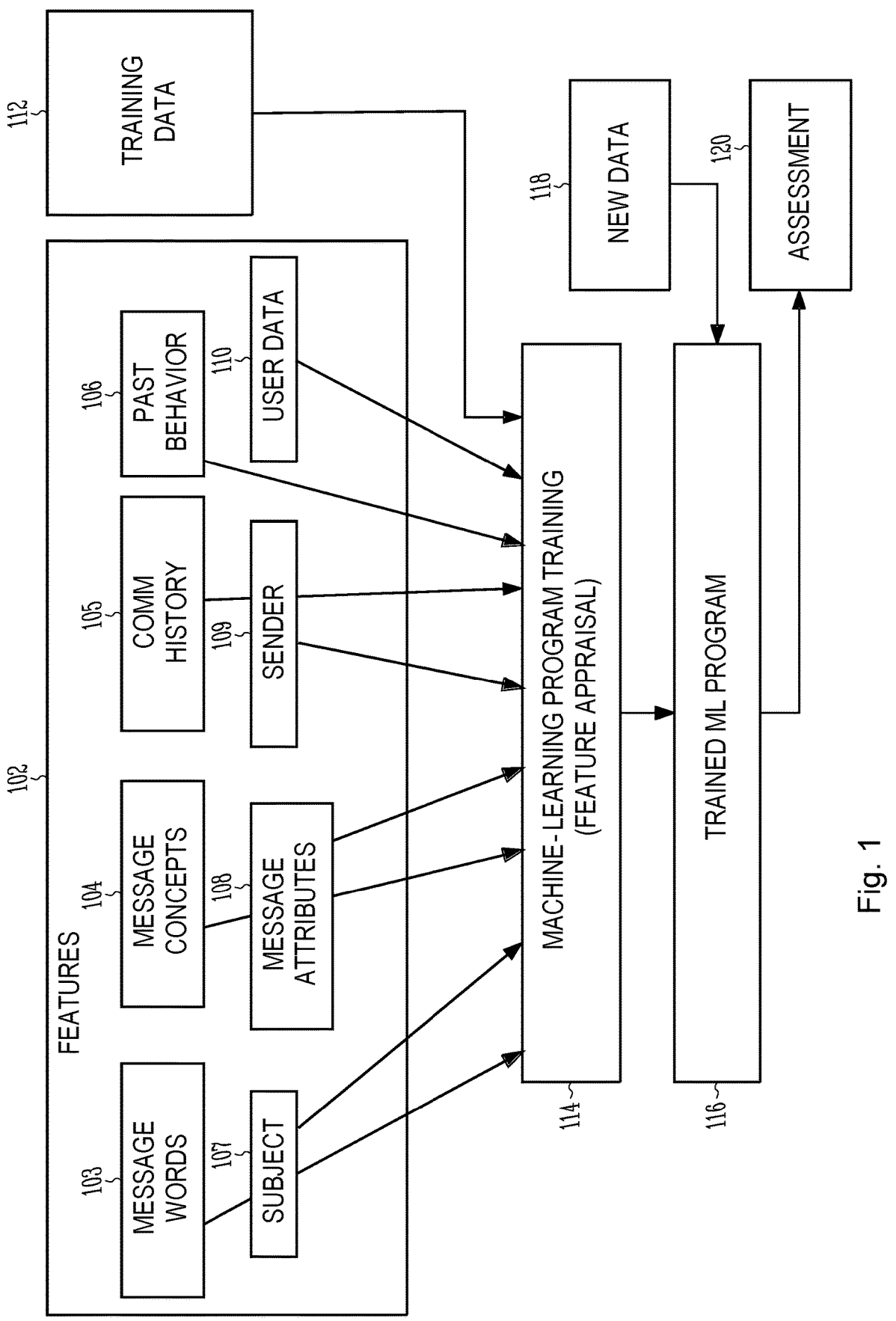
FIG. 1 illustrates the training and use of a machine-learning program, in accordance with some implementations.

The following description and the drawings sufficiently illustrate specific implementations to enable those skilled in the art to practice them. Other implementations may incorporate structural, logical, electrical, process, and other changes. Portions and features of some implementations may be included in, or substituted for, those of other implementations. Implementations set forth in the claims encompass all available equivalents of those claims.

According to some implementations, a system can include an automated sample analyzer that comprises: a sample input device receiving a liquid sample, a sample analyzing device reading measurements associated with the liquid sample, a display device displaying a graphical user interface (GUI) to a current user of the automated sample analyzer, the GUI being for controlling or maintaining the automated sample analyzer by the current user, processing circuitry, and a memory. The memory stores a receiving engine receiving the measurements associated with the liquid sample from the sample analyzing device and storing the received measurements in memory. The memory stores a configuration control engine which, when executed by the processing circuitry, causes the processing circuitry to set a configuration of a user model to correspond to the current user of the automated sample analyzer. The memory stores a learning engine which, when executed by the processing circuitry, causes the processing circuitry to detect and collect at least one pattern of interaction of the current user with the GUI. The memory stores a user interface engine which, when executed by the processing circuitry, causes the processing circuitry to configure the GUI according to user-dependent configuration data of the configuration of the user model corresponding to the current user, the user-dependent configuration data being received from a user data repository.

Some implementations include a machine-readable medium storing all or a portion of the data and instructions stored in the memory. Some implementations include a method for performing all or a portion of the techniques described above. Some implementations include an apparatus comprising means for performing all or a portion of the techniques described above.

DETAILED DESCRIPTION

The following description and the drawings sufficiently illustrate specific implementations to enable those skilled in the art to practice them. Other implementations may incorporate structural, logical, electrical, process, and other changes. Portions and features of some implementations may be included in, or substituted for, those of other implementations. Implementations set forth in the claims encompass all available equivalents of those claims.

Automated sample analyzers for analyzing liquid samples are, oftentimes, used by many different people (e.g., scientific researchers, lab technicians, repair persons, and the like) with different use cases. However, the automated sample analyzer may provide the same series of user interfaces with the same selectable user interface elements for each and every user resulting in a fixed configuration for each user of the automated sample analyzer. This makes the user experience of using the automated sample analyzer not user-friendly, as the user might have to go through several different menus to perform a task that he/she performs regularly. That is, a user may have to navigate through one or more user interfaces that are not related to the task being performed by the user. For example, due to the fixed configuration of menus and user interface elements of the automated sample analyzer, a user performing maintenance on the automated sample analyzer may navigate through one or more user interfaces related to analyzing samples before reaching a user interface used to perform maintenance on the automated sample analyzer. Additionally, a user operating the automated sample analyzer to analyze a first type of sample may navigate through one or more user interfaces corresponding to the analysis of a second type of sample before accessing a user interface configured to analyze the first type of sample. As the foregoing illustrates, a more user-friendly user interface for the automated sample analyzer, which is tailored to the current user, is desirable.

Further, the implementations described herein can provide a level of traceability of actions taken by users of the automated sample analyzer that is not present in existing systems. For example, in existing systems, since actions performed by users are not monitored or tracked using image recognition techniques and/or machine learning techniques, actions related to the testing of sample, calibration of analyzers, and/or maintenance of analyzers can be performed without the user performing the actions being identified in the system. The systems, analyzers, methods, and techniques described herein can be used to monitor actions performed by each user of the automated sample analyzer and enable entities using the automated sample analyzers to trace actions back to one or more users in order to comply with internal or external requirements.

Some implementations are directed to a user-friendly automated sample analyzer. To illustrate, interactions of individual users of the automated sample analyzer can be analyzed using machine learning techniques to determine a pattern of interaction of an individual user with the automated sample analyzer. The pattern of interaction can include a series of user interfaces accessed by the individual user. Additionally, the pattern of interaction can include user interface elements selected by the individual users during operation of the automated sample analyzer. The pattern of interaction can be used to determine a customized configuration of the automated sample analyzer for the individual user that minimizes the time spent by the user accessing menus and user interfaces of the automated sample analyzer to perform operations related to actions to be accomplished by the individual user with the automated sample analyzer. As a result, individual users can more efficiently operate the sample analyzer and workflows for users of the sample analyzer can be developed that are more efficient that workflows of existing analyzers.

According to some implementations, an automated sample analyzer comprises: a sample input device receiving a liquid sample, a sample analyzing device reading measurements associated with the liquid sample, a display device displaying a graphical user interface (GUI) to a current user of the automated sample analyzer, the GUI being for controlling or maintaining the automated sample analyzer by the current user, processing circuitry, and a memory. The memory stores a receiving engine receiving the measurements associated with the liquid sample from the sample analyzing device and storing the received measurements in memory. The memory stores a configuration control engine which, when executed by the processing circuitry, causes the processing circuitry to set a configuration of a user model to correspond to the current user of the automated sample analyzer. The memory stores a learning engine which, when executed by the processing circuitry, causes the processing circuitry to detect and collect at least one pattern of interaction of the current user with the GUI. The memory stores a user interface engine which, when executed by the processing circuitry, causes the processing circuitry to configure the GUI according to user-dependent configuration data of the configuration of the user model corresponding to the current user, the user-dependent configuration data being received from a user data repository.

The learning engine, when executed by the processing circuitry, causes the processing circuitry to: identify an accessing user and, upon validation, establish the accessing user as the current user; monitor interaction between the current user and the GUI and store interaction data of the current user in association with time; determine, based on the interaction data, at least one time-cyclical pattern of interaction between the current user and the GUI; and store the at least one time-cyclical pattern of interaction.

The configuration control engine, when executed by the processing circuitry, causes the processing circuitry to: identify the accessing user and, upon validation, establish the accessing user as the current user; determine, based on a current time and the stored at least one time-cyclical pattern of interaction, a pattern of interaction for the current time; and display, within the GUI, a shortcut to implement the pattern of interaction for the current time. In some cases, processing circuitry forgoes displaying the shortcut in response to a user request. The configuration control engine may operate asynchronously (e.g., at a different time) with the learning engine.

As used herein, the phrase "time-cyclical pattern" encompasses its plain and ordinary meaning and may include, for example, patterns that are cyclical based on time of day, day of the week, day of the month, and the like. For example, a user may open the automated sample analyzer for cleaning on the first Thursday afternoon of every month, or load reagents into the automated sample analyzer every Tuesday morning.

Aspects of the present disclosure may be implemented as part of a computer system. The computer system may be one physical machine, or may be distributed among multiple physical machines, such as by role or function, or by process thread in the case of a cloud computing distributed model. In various implementations, aspects of the invention may be configured to run in virtual machines that in turn are executed on one or more physical machines. It will be understood by persons of skill in the art that features of the invention may be realized by a variety of different suitable machine implementations.

The system includes various engines, each of which is constructed, programmed, configured, or otherwise adapted, to carry out a function or set of functions. The term engine as used herein means a tangible device, component, or arrangement of components implemented using hardware, such as by an application specific integrated circuit (ASIC) or field-programmable gate array (FPGA), for example, or as a combination of hardware and software, such as by a processor-based computing platform and a set of program instructions that transform the computing platform into a special-purpose device to implement the particular functionality. An engine may also be implemented as a combination of the two, with certain functions facilitated by hardware alone, and other functions facilitated by a combination of hardware and software.

In an example, the software may reside in executable or non-executable form on a tangible machine-readable storage medium. Software residing in non-executable form may be compiled, translated, or otherwise converted to an executable form prior to, or during, runtime. In an example, the software, when executed by the underlying hardware of the engine, causes the hardware to perform the specified operations. Accordingly, an engine is physically constructed, or specifically configured (e.g., hardwired), or temporarily configured (e.g., programmed) to operate in a specified manner or to perform part or all of any operations described herein in connection with that engine.

Considering examples in which engines are temporarily configured, each of the engines may be instantiated at different moments in time. For example, where the engines comprise a general-purpose hardware processor core configured using software; the general-purpose hardware processor core may be configured as respective different engines at different times. Software may accordingly configure a hardware processor core, for example, to constitute a particular engine at one instance of time and to constitute a different engine at a different instance of time.

In certain implementations, at least a portion, and in some cases, all, of an engine may be executed on the processor(s) of one or more computers that execute an operating system, system programs, and application programs, while also implementing the engine using multitasking, multithreading, distributed (e.g., cluster, peer-peer, cloud, etc.) processing where appropriate, or other such techniques. Accordingly, each engine may be realized in a variety of suitable configurations, and should generally not be limited to any particular implementation exemplified herein, unless such limitations are expressly called out.

In addition, an engine may itself be composed of more than one sub-engines, each of which may be regarded as an engine in its own right. Moreover, in the implementations described herein, each of the various engines corresponds to a defined functionality; however, it should be understood that in other contemplated implementations, each functionality may be distributed to more than one engine. Likewise, in other contemplated implementations, multiple defined functionalities may be implemented by a single engine that performs those multiple functions, possibly alongside other functions, or distributed differently among a set of engines than specifically illustrated in the examples herein.

FIG. 1 illustrates the training and use of a machine-learning program, according to some example implementations. In some example implementations, machine-learning programs (MLPs), also referred to as machine-learning algorithms or tools, are utilized to perform operations associated with machine learning tasks, such as image recognition or machine translation.

Machine learning is a field of study that gives computers the ability to learn without being explicitly programmed. Machine learning explores the study and construction of algorithms, also referred to herein as tools, which may learn from existing data and make predictions about new data. Such machine-learning tools operate by building a model from example training data 112 in order to make data-driven predictions or decisions expressed as outputs or assessments 120. Although example implementations are presented with respect to a few machine-learning tools, the principles presented herein may be applied to other machine-learning tools.

In some example implementations, different machine-learning tools may be used. For example, Logistic Regression (LR), Naive-Bayes, Random Forest (RF), neural networks (NN), matrix factorization, and Support Vector Machines (SVM) tools may be used for classifying or scoring job postings.

Two common types of problems in machine learning are classification problems and regression problems. Classification problems, also referred to as categorization problems, aim at classifying items into one of several category values (for example, is this object an apple or an orange). Regression algorithms aim at quantifying some items (for example, by providing a value that is a real number). The machine-learning algorithms utilize the training data 112 to find correlations among identified features 102 that affect the outcome.

The machine-learning algorithms utilize features 102 for analyzing the data to generate assessments 120. A feature 102 is an individual measurable property of a phenomenon being observed. The concept of a feature is related to that of an explanatory variable used in statistical techniques such as linear regression. Choosing informative, discriminating, and independent features is important for effective operation of the MLP in pattern recognition, classification, and regression. Features may be of different types, such as numeric features, strings, and graphs.

In one example implementation, the features 102 may be of different types and may include one or more of words of the message 103, message concepts 104, communication history 105, past user behavior 106, subject of the message 107, other message attributes 108, sender 109, and user data 110.

The machine-learning algorithms utilize the training data 112 to find correlations among the identified features 102 that affect the outcome or assessment 120. In some example implementations, the training data 112 includes labeled data, which is known data for one or more identified features 102 and one or more outcomes, such as detecting communication patterns, detecting the meaning of the message, generating a summary of the message, detecting action items in the message, detecting urgency in the message, detecting a relationship of the user to the sender, calculating score attributes, calculating message scores, etc.

With the training data 112 and the identified features 102, the machine-learning tool is trained at operation 114. The machine-learning tool appraises the value of the features 102 as they correlate to the training data 112. The result of the training is the trained machine-learning program 116.

When the machine-learning program 116 is used to perform an assessment, new data 118 is provided as an input to the trained machine-learning program 116, and the machine-learning program 116 generates the assessment 120 as output. For example, when a message is checked for an action item, the machine-learning program utilizes the message content and message metadata to determine if there is a request for an action in the message.

Machine learning techniques train models to accurately make predictions on data fed into the models (e.g., what was said by a user in a given utterance; whether a noun is a person, place, or thing; what the weather will be like tomorrow). During a learning phase, the models are developed against a training dataset of inputs to optimize the models to correctly predict the output for a given input. Generally, the learning phase may be supervised, semi-supervised, or unsupervised; indicating a decreasing level to which the "correct" outputs are provided in correspondence to the training inputs. In a supervised learning phase, all of the outputs are provided to the model and the model is directed to develop a general rule or algorithm that maps the input to the output. In contrast, in an unsupervised learning phase, the desired output is not provided for the inputs so that the model may develop its own rules to discover relationships within the training dataset. In a semi-supervised learning phase, an incompletely labeled training set is provided, with some of the outputs known and some unknown for the training dataset.

Models may be run against a training dataset for several epochs (e.g., iterations), in which the training dataset is repeatedly fed into the model to refine its results. For example, in a supervised learning phase, a model is developed to predict the output for a given set of inputs, and is evaluated over several epochs to more reliably provide the output that is specified as corresponding to the given input for the greatest number of inputs for the training dataset. In another example, for an unsupervised learning phase, a model is developed to cluster the dataset into n groups, and is evaluated over several epochs as to how consistently it places a given input into a given group and how reliably it produces the n desired clusters across each epoch.

Once an epoch is run, the generated predictions are evaluated and the values of their variables are adjusted to attempt to better refine the predictions in an iterative fashion. In various aspects, the evaluations are biased against false negatives, biased against false positives, or evenly biased with respect to the overall accuracy of the model. The values may be adjusted in several ways depending on the machine learning technique used. For example, in a genetic or evolutionary algorithm, the values for the models that are most successful in predicting the desired outputs are used to develop values for models to use during the subsequent epoch, which may include random variation/mutation to provide additional data points. One of ordinary skill in the art will be familiar with several other machine learning algorithms that may be applied with the present disclosure, including linear regression, random forests, decision tree learning, neural networks, deep neural networks, etc.

Each model develops a rule or algorithm over several epochs by varying the values of one or more variables affecting the inputs to more closely map to a desired result, but as the training dataset may be varied, and is preferably very large, perfect accuracy and precision may not be achievable. A number of episodes that make up a learning phase, therefore, may be set as a given number of trials or a fixed time/computing budget, or may be terminated before that number/budget is reached when the accuracy of a given model is high enough or low enough or an accuracy plateau has been reached. For example, if the training phase is designed to run n epochs and produce a model with at least 95% accuracy, and such a model is produced before the $n^{th}$ epoch, the learning phase may end early and use the produced model satisfying the end-goal accuracy threshold. Similarly, if a given model is inaccurate enough to satisfy a random chance threshold (e.g., the model is only 55% accurate in determining true/false outputs for given inputs), the learning phase for that model may be terminated early, although other models in the learning phase may continue training. Similarly, when a given model continues to provide similar accuracy or vacillate in its results across multiple epochs—having reached a performance plateau—the learning phase for the given model may terminate before the epoch number/computing budget is reached.

Once the learning phase is complete, the models are finalized. In some example implementations, models that are finalized are evaluated against testing criteria. In a first example, a testing dataset that includes known outputs for its inputs is fed into the finalized models to determine an accuracy of the model in handling data that is has not been trained on. In a second example, a false positive rate or false negative rate may be used to evaluate the models after finalization. In a third example, a delineation between data clusterings is used to select a model that produces the clearest bounds for its clusters of data.

Figure 2:
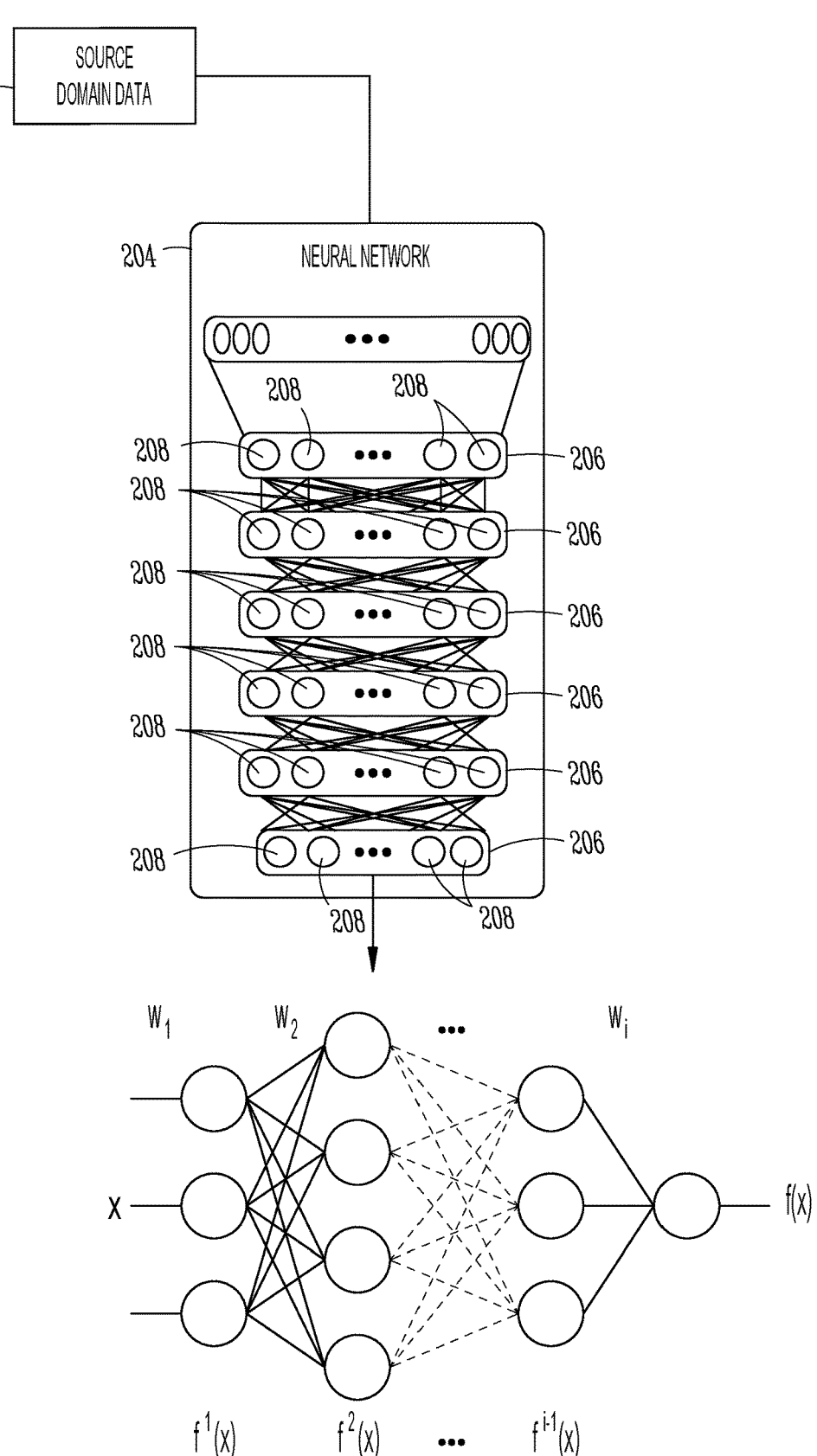
FIG. 2 illustrates an example neural network, in accordance with some implementations.

FIG. 2 illustrates an example neural network 204, in accordance with some implementations. As shown, the neural network 204 receives, as input, source domain data 202. The input is passed through a plurality of layers 206 to arrive at an output. Each layer 206 includes multiple neurons 208. The neurons 208 receive input from neurons of a previous layer and apply weights to the values received from those neurons in order to generate a neuron output. The neuron outputs from the final layer 206 are combined to generate the output of the neural network 204.

As illustrated at the bottom of FIG. 2, the input is a vector x. The input is passed through multiple layers 206, where weights $W_1$, $W_2$, . . . , $W_i$ are applied to the input to each layer to arrive at $f^1(x)$, $f^2(x)$, . . . , $f^{i-1}(x)$, until finally the output $f(x)$ is computed.

In some example implementations, the neural network 204 (e.g., deep learning, deep convolutional, or recurrent neural network) comprises a series of neurons 208, such as Long Short Term Memory (LSTM) nodes, arranged into a network. A neuron 208 is an architectural element used in data processing and artificial intelligence, particularly machine learning, which includes memory that may determine when to "remember" and when to "forget" values held in that memory based on the weights of inputs provided to the given neuron 208. Each of the neurons 208 used herein are configured to accept a predefined number of inputs from other neurons 208 in the neural network 204 to provide relational and sub-relational outputs for the content of the frames being analyzed. Individual neurons 208 may be chained together and/or organized into tree structures in various configurations of neural networks to provide interactions and relationship learning modeling for how each of the frames in an utterance is related to one another.

For example, an LSTM node serving as a neuron includes several gates to handle input vectors (e.g., phonemes from an utterance), a memory cell, and an output vector (e.g., contextual representation). The input gate and output gate control the information flowing into and out of the memory cell, respectively, whereas forget gates optionally remove information from the memory cell based on the inputs from linked cells earlier in the neural network. Weights and bias vectors for the various gates are adjusted over the course of a training phase, and once the training phase is complete, those weights and biases are finalized for normal operation. One of skill in the art will appreciate that neurons and neural networks may be constructed programmatically (e.g., via software instructions) or via specialized hardware linking each neuron to form the neural network.

Neural networks utilize features for analyzing the data to generate assessments (e.g., recognize units of speech). A feature is an individual measurable property of a phenomenon being observed. The concept of feature is related to that of an explanatory variable used in statistical techniques such as linear regression. Further, deep features represent the output of nodes in hidden layers of the deep neural network.

A neural network, sometimes referred to as an artificial neural network, is a computing system/apparatus based on consideration of biological neural networks of animal brains. Such systems/apparatus progressively improve performance, which is referred to as learning, to perform tasks, typically without task-specific programming. For example, in image recognition, a neural network may be taught to identify images that contain an object by analyzing example images that have been tagged with a name for the object and, having learnt the object and name, may use the analytic results to identify the object in untagged images. A neural network is based on a collection of connected units called neurons, where each connection between neurons can transmit a unidirectional signal with an activating strength that varies with the strength of the connection. The receiving neuron can activate and propagate a signal to downstream neurons connected to it, typically based on whether the combined incoming signals, which are from potentially many transmitting neurons, are of sufficient strength, where strength is a parameter.

A deep neural network (DNN) is a stacked neural network, which is composed of multiple layers. The layers are composed of nodes, which are locations where computation occurs, loosely patterned on a neuron in the human brain, which fires when it encounters sufficient stimuli. A node combines input from the data with a set of coefficients, or weights, that either amplify or dampen that input, which assigns significance to inputs for the task the algorithm is trying to learn. These input-weight products are summed, and the sum is passed through what is called a node's activation function, to determine whether and to what extent that signal progresses further through the network to affect the ultimate outcome. A DNN uses a cascade of many layers of non-linear processing units for feature extraction and transformation. Each successive layer uses the output from the previous layer as input. Higher-level features are derived from lower-level features to form a hierarchical representation. The layers following the input layer may be convolution layers that produce feature maps that are filtering results of the inputs and are used by the next convolution layer.

In training of a DNN architecture, a regression, which is structured as a set of statistical processes for estimating the relationships among variables, can include a minimization of a cost function. The cost function may be implemented as a function to return a number representing how well the neural network performed in mapping training examples to correct output. In training, if the cost function value is not within a pre-determined range, based on the known training images, backpropagation is used, where backpropagation is a common method of training artificial neural networks that are used with an optimization method such as a stochastic gradient descent (SGD) method.

Use of backpropagation can include propagation and weight update. When an input is presented to the neural network, it is propagated forward through the neural network, layer by layer, until it reaches the output layer. The output of the neural network is then compared to the desired output, using the cost function, and an error value is calculated for each of the nodes in the output layer. The error values are propagated backwards, starting from the output, until each node has an associated error value which roughly represents its contribution to the original output. Backpropagation can use these error values to calculate the gradient of the cost function with respect to the weights in the neural network. The calculated gradient is fed to the selected optimization method to update the weights to attempt to minimize the cost function.

Figure 3:
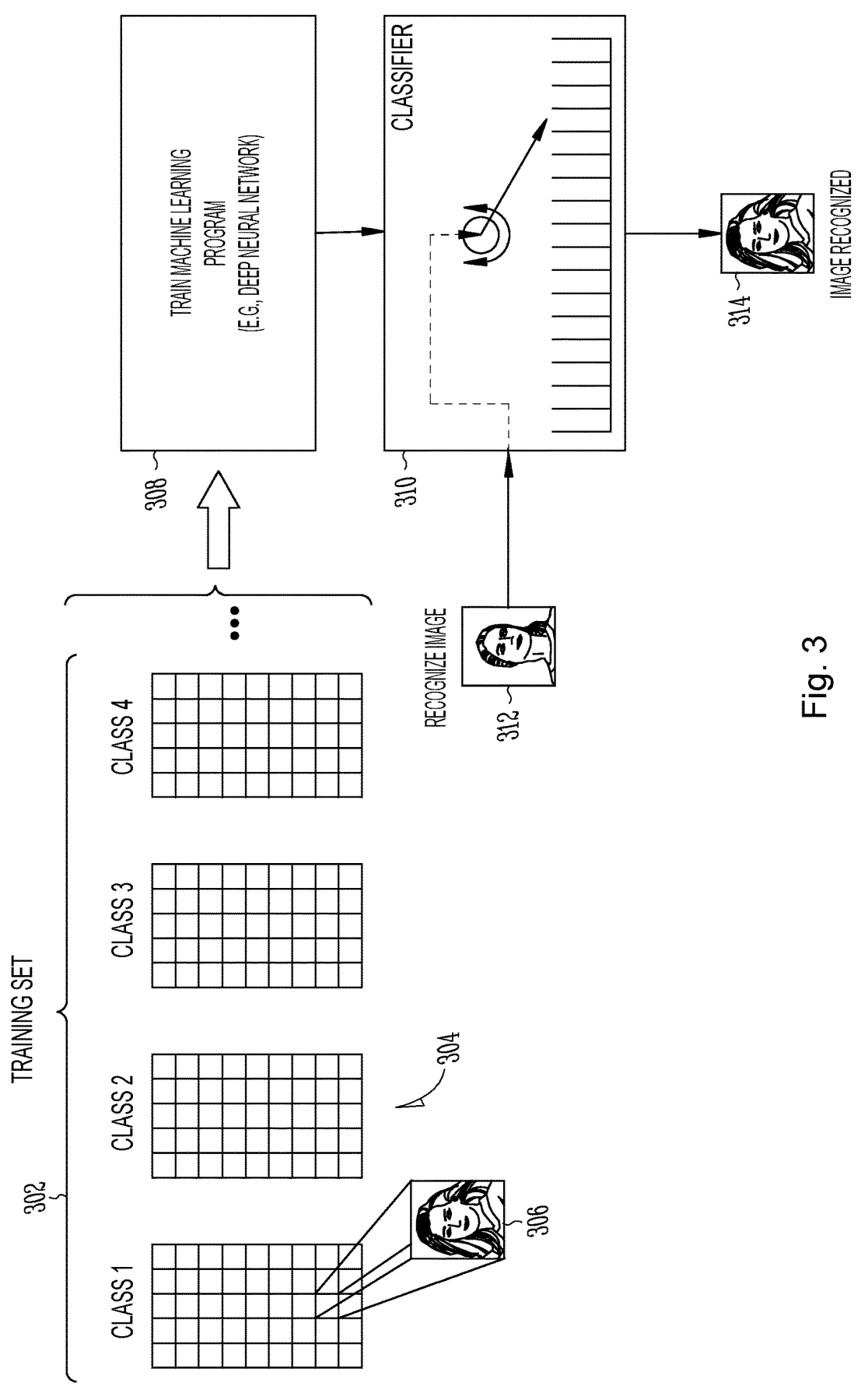
FIG. 3 illustrates the training of an image recognition machine learning program, in accordance with some implementations.

FIG. 3 illustrates the training of an image recognition machine learning program, in accordance with some implementations. The machine learning program may be implemented at one or more computing machines. Block 302 illustrates a training set, which includes multiple classes 304. Each class 304 includes multiple images 306 associated with the class. Each class 304 may correspond to a type of object in the image 306 (e.g., a digit 0-9, a man or a woman, a cat or a dog, etc.). In one example, the machine learning program is trained to recognize images of the presidents of the United States, and each class corresponds to each president (e.g., one class corresponds to Barack Obama, one class corresponds to George W. Bush, etc.). At block 308 the machine learning program is trained, for example, using a deep neural network. At block 310, the trained classifier, generated by the training of block 308, recognizes an image 312, and at block 314 the image is recognized. For example, if the image 312 is a photograph of Bill Clinton, the classifier recognizes the image as corresponding to Bill Clinton at block 314.

Figure 4:
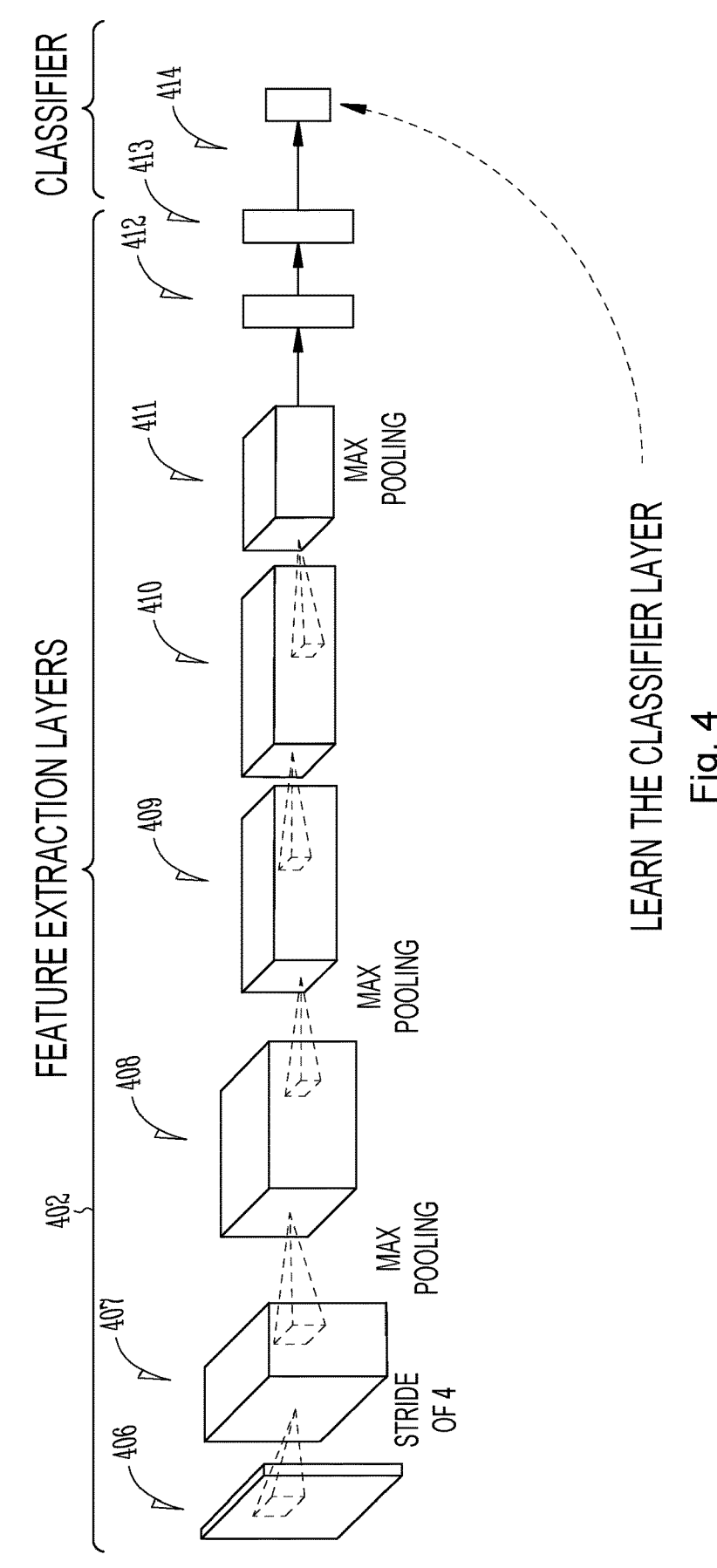
FIG. 4 illustrates the feature-extraction process and classifier training, in accordance with some implementations.

FIG. 4 illustrates the feature-extraction process and classifier training, according to some example implementations. Training the classifier may be divided into feature extraction layers 402 and classifier layer 414. Each image is analyzed in sequence by a plurality of layers 406-413 in the feature-extraction layers 402.

With the development of deep convolutional neural networks, the focus in face recognition has been to learn a good face feature space, in which faces of the same person are close to each other, and faces of different persons are far away from each other. For example, the verification task with the LFW (Labeled Faces in the Wild) dataset has been often used for face verification.

Many face identification tasks (e.g., MegaFace and LFW) are based on a similarity comparison between the images in the gallery set and the query set, which is essentially a K-nearest-neighborhood (KNN) method to estimate the person's identity. In the ideal case, there is a good face feature extractor (inter-class distance is always larger than the intra-class distance), and the KNN method is adequate to estimate the person's identity.

Feature extraction is a process to reduce the amount of resources required to describe a large set of data. When performing analysis of complex data, one of the major problems stems from the number of variables involved. Analysis with a large number of variables generally requires a large amount of memory and computational power, and it may cause a classification algorithm to overfit to training samples and generalize poorly to new samples. Feature extraction is a general term describing methods of constructing combinations of variables to get around these large data-set problems while still describing the data with sufficient accuracy for the desired purpose.

In some example implementations, feature extraction starts from an initial set of measured data and builds derived values (features) intended to be informative and non-redundant, facilitating the subsequent learning and generalization steps. Further, feature extraction is related to dimensionality reduction, such as be reducing large vectors (sometimes with very sparse data) to smaller vectors capturing the same, or similar, amount of information.

Determining a subset of the initial features is called feature selection. The selected features are expected to contain the relevant information from the input data, so that the desired task can be performed by using this reduced representation instead of the complete initial data. DNN utilizes a stack of layers, where each layer performs a function. For example, the layer could be a convolution, a non-linear transform, the calculation of an average, etc. Eventually this DNN produces outputs by classifier 414. In FIG. 4, the data travels from left to right and the features are extracted. The goal of training the neural network is to find the parameters of all the layers that make them adequate for the desired task.

As shown in FIG. 4, a "stride of 4" filter is applied at layer 406, and max pooling is applied at layers 407-413. The stride controls how the filter convolves around the input volume. "Stride of 4" refers to the filter convolving around the input volume four units at a time. Max pooling refers to down-sampling by selecting the maximum value in each max pooled region.

In some example implementations, the structure of each layer is predefined. For example, a convolution layer may contain small convolution kernels and their respective convolution parameters, and a summation layer may calculate the sum, or the weighted sum, of two pixels of the input image. Training assists in defining the weight coefficients for the summation.

One way to improve the performance of DNNs is to identify newer structures for the feature-extraction layers, and another way is by improving the way the parameters are identified at the different layers for accomplishing a desired task. The challenge is that for a typical neural network, there may be millions of parameters to be optimized. Trying to optimize all these parameters from scratch may take hours, days, or even weeks, depending on the amount of computing resources available and the amount of data in the training set.

Figure 5:
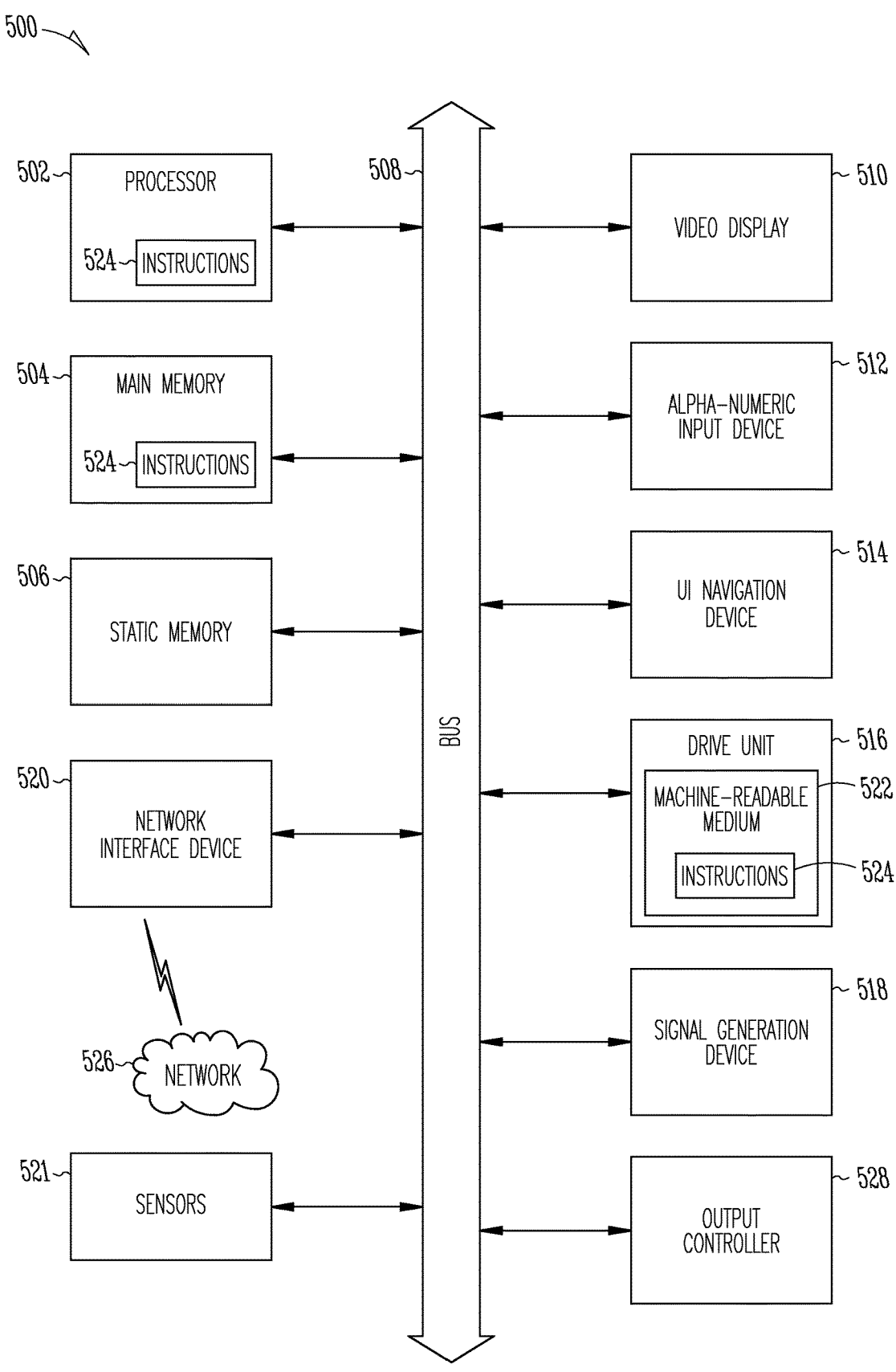
FIG. 5 is a block diagram of a computing machine, in accordance with some implementations.

FIG. 5 illustrates a circuit block diagram of a computing machine 500 in accordance with some implementations. In some implementations, components of the computing machine 500 may store or be integrated into other components shown in the circuit block diagram of FIG. 5. For example, portions of the computing machine 500 may reside in the processor 502 and may be referred to as "processing circuitry." Processing circuitry may include processing hardware, for example, one or more central processing units (CPUs), one or more graphics processing units (GPUs), and the like. In alternative implementations, the computing machine 500 may operate as a standalone device or may be connected (e.g., networked) to other computers. In a networked deployment, the computing machine 500 may operate in the capacity of a server, a client, or both in server-client network environments. In an example, the computing machine 500 may act as a peer machine in peer-to-peer (P2P) (or other distributed) network environment. In this document, the phrases P2P, device-to-device (D2D) and sidelink may be used interchangeably. The computing machine 500 may be a specialized computer, a personal computer (PC), a tablet PC, a personal digital assistant (PDA), a mobile telephone, a smart phone, a web appliance, a network router, switch or bridge, or any machine capable of executing instructions (sequential or otherwise) that specify actions to be taken by that machine.

Examples, as described herein, may include, or may operate on, logic or a number of components, modules, or mechanisms. Modules and components are tangible entities (e.g., hardware) capable of performing specified operations and may be configured or arranged in a certain manner. In an example, circuits may be arranged (e.g., internally or with respect to external entities such as other circuits) in a specified manner as a module. In an example, the whole or part of one or more computer systems/apparatus (e.g., a standalone, client or server computer system) or one or more hardware processors may be configured by firmware or software (e.g., instructions, an application portion, or an application) as a module that operates to perform specified operations. In an example, the software may reside on a machine readable medium. In an example, the software, when executed by the underlying hardware of the module, causes the hardware to perform the specified operations.

Accordingly, the term "module" (and "component") is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor may be configured as respective different modules at different times. Software may accordingly configure a hardware processor, for example, to constitute a particular module at one instance of time and to constitute a different module at a different instance of time.

The computing machine 500 may include a hardware processor 502 (e.g., a central processing unit (CPU), a GPU, a hardware processor core, or any combination thereof), a main memory 504 and a static memory 506, some or all of which may communicate with each other via an interlink (e.g., bus) 508. Although not shown, the main memory 504 may contain any or all of removable storage and non-removable storage, volatile memory or non-volatile memory. The computing machine 500 may further include a video display unit 510 (or other display unit), an alphanumeric input device 512 (e.g., a keyboard), and a user interface (UI) navigation device 514 (e.g., a mouse). In an example, the display unit 510, input device 512 and UI navigation device 514 may be a touch screen display. The computing machine 500 may additionally include a storage device (e.g., drive unit) 516, a signal generation device 518 (e.g., a speaker), a network interface device 520, and one or more sensors 521, such as a global positioning system (GPS) sensor, compass, accelerometer, or other sensor. The computing machine 500 may include an output controller 528, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The drive unit 516 (e.g., a storage device) may include a machine readable medium 522 on which is stored one or more sets of data structures or instructions 524 (e.g., software) embodying or utilized by any one or more of the techniques or functions described herein. The instructions 524 may also reside, completely or at least partially, within the main memory 504, within static memory 506, or within the hardware processor 502 during execution thereof by the computing machine 500. In an example, one or any combination of the hardware processor 502, the main memory 504, the static memory 506, or the storage device 516 may constitute machine readable media.

While the machine readable medium 522 is illustrated as a single medium, the term "machine readable medium" may include a single medium or multiple media (e.g., a centralized or distributed database, and/or associated caches and servers) configured to store the one or more instructions 524.

The term "machine readable medium" may include any medium that is capable of storing, encoding, or carrying instructions for execution by the computing machine 500 and that cause the computing machine 500 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; Random Access Memory (RAM); and CD-ROM and DVD-ROM disks. In some examples, machine readable media may include non-transitory machine readable media. In some examples, machine readable media may include machine readable media that is not a transitory propagating signal.

The instructions 524 may further be transmitted or received over a communications network 526 using a transmission medium via the network interface device 520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, a Long Term Evolution (LTE) family of standards, a Universal Mobile Telecommunications System (UMTS) family of standards, peer-to-peer (P2P) networks, among others. In an example, the network interface device 520 may include one or more physical jacks (e.g., Ethernet, coaxial, or phone jacks) or one or more antennas to connect to the communications network 526.

Figure 6:
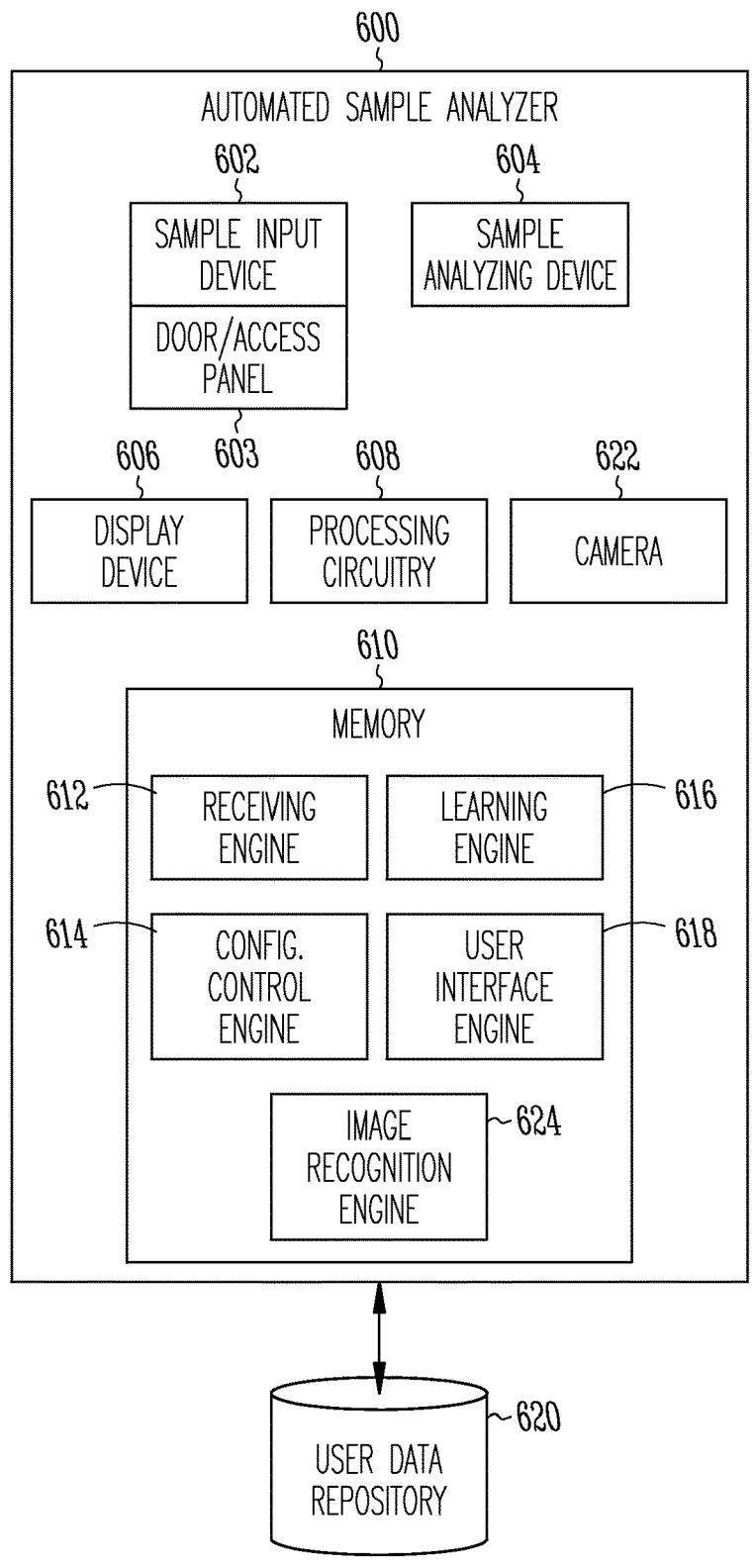
FIG. 6 is a block diagram of an automated sample analyzer, in accordance with some implementations.

FIG. 6 is a block diagram of an automated sample analyzer 600, in accordance with some implementations. As shown, the automated sample analyzer 600 is communicatively coupled (e.g., via a network or other connection) with a user data repository 620. In alternative implementations, the user data repository 620 may reside within the automated sample analyzer 600 (e.g., within the memory 610). The user data repository 620 stores information about users of the automated sample analyzer 600. The user data repository 620 may be a database.

The automated sample analyzer 600 includes a sample input device 602, a sample analyzing device 604, a display device 606, a camera 622, processing circuitry 608, and memory 610. The sample input device 602 receives a liquid sample (or multiple liquid samples). As shown, the sample input device 602 may include or be coupled with a door or an access panel 603. The sample analyzing device 604 takes and reads measurements associated with the liquid sample. The display device 606 (e.g., a monitor or a screen) displays a GUI to a current user of the automated sample analyzer 600. The GUI is for controlling or maintaining the automated sample analyzer 600 by the current user. The processing circuitry 608 may include one or more hardware processors, which may be configured in a processing unit, for example, a central processing unit (CPU) or a graphics processing unit (GPU). The camera 622 receives image data, which may be processed by the processing circuitry 608 using instructions stored in the memory 610.

The memory 610 may include a cache unit or a storage unit. The memory 610 may include a non-transitory machine-readable medium. As shown, the memory 610 stores a receiving engine 612, a configuration (config) control engine 614, a learning engine 616, a user interface engine 618, and an image recognition engine 624. The receiving engine 612, when executed, receives the measurements associated with the liquid sample from the sample analyzing device 604 and stores the received measurements in the memory 610. The configuration control engine 614, when executed, sets a configuration of a user model to correspond to the current user of the automated sample analyzer 600. The configuration control engine 614 causes the processing circuitry 608 to perform the method 700 shown in FIG. 7. The learning engine 616, when executed, detects and collects at least one pattern of interaction of the current user with the GUI. The learning engine 616 causes the processing circuitry 608 to perform the method 800 shown in FIG. 8. The user interface engine 618, when executed, configures the GUI according to user-dependent configuration data of the configuration of the user model corresponding to the current user. The user-dependent configuration data is received from a user data repository 620.

The learning engine 616 may include an artificial neural network. The artificial neural network may establish a correlation between the pattern of interaction with the current user, a history of interaction with the current user, and the configuration of the user model. Alternatively, a statistical model may establish the correlation between the pattern of interaction with the current user, the history of interaction with the current user, and the configuration of the user model.

In some implementations, the learning engine 616 provides an output representing changes made to the user model and requests feedback, via the GUI, from the current user on the changes made to the user model. In some implementations, the learning engine 616 provides an output (e.g., in a pop-up window) representing previous actions of the current user via the GUI. In some implementations, the learning engine 616 generates an output representing previous actions that were previously presented in a menu that are not included in a corresponding set of current actions that were not previously presented in the menu. In some implementations, the learning engine 616 predicts a next action by image recognition (e.g., by a camera taking an image of an object the user is holding, which is identified using image recognition, and/or by using a high frequency menu in the stored previous actions by the same user by the same time slot at the same time in a time cycle (e.g., same time of day or day of the week)). In some implementations, the learning engine 616 provides an output instructing the current user about operating at least some hardware of the automated sample analyzer 600.

In some implementations, the learning engine 616 provides an output instructing the current user how to operate hardware of the automated sample analyzer. The hardware of the automated sample analyzer may include or be coupled with a door/access panel 603 for reagent loading (see, e.g., block 1312 of FIG. 13) into the sample input device 602 (see, e.g., block 1310 of FIG. 13). In some implementations, the learning engine 616 shows the previous actions in a diagram displayed in the GUI. The GUI may provide an interface for user selection (e.g., by clicking a mouse or touching a touchscreen of the display device 606) of one or more of the previous actions for demonstration in the diagram.

The learning engine 616 may determine impairment of the current user, for example by monitoring the current user's reaction time, instability (e.g., jitteriness) of action of the input device, dilated eyes (with the facial recognition camera), excessive incorrect menu picks or by using any other impairment test. A report of the impairment of the current user may be transmitted (e.g., to a supervisor of the current user) by the processing circuitry 608 implementing the learning engine 616 if a predetermined level of impairment is detected.

In some implementations, the user-dependent configuration data includes menu optimization data that defines a menu optimization comprising a set of menus for presentation within the GUI or a set of menu items for presentation within the menus of the GUI. The menu optimization data may be derived from prior menu usage or prior menu item usage of the current user, for example, by artificial intelligence menu usage review of the prior menu usage or prior menu item usage of the current user. Specifically, an artificial intelligence engine may analyze a prior menu usage frequency of the current user to generate the user-dependent configuration data. In some examples, the techniques shown in FIGS. 1-4 are used to derive the menu optimization data. The menu optimization may be implemented automatically, without prompting the current user to cause menu optimization. Alternatively, this may be done responsive to a user request for menu optimization. The automated sample analyzer 600 may: display an optimized menu; receive, via the GUI, a request to revert to a prior version of the menu; and responsive to the request, display the prior version of the menu. The artificial intelligence engine may compute a user productivity value and correlate the user productivity value with at least one metric (e.g., uptime of the automated sample analyzer 600, reliability of the automated sample analyzer 600, reliability of the automated sample analyzer 600, and the like).

In some cases, the new user-dependent configuration data that is updated in the user data repository 620 comprises different GUI configurations for different times with at least a first GUI configuration for a first time range and a second GUI configuration for a second time range. In some cases, the different GUI configurations for different times are determined based on interaction between the current user and the GUI within a predetermined number of days. The first time range or the second time range may be a time of day (e.g., 12 pm-3 pm) or a day of the week (e.g., Monday). The user may be able to drag/change the time range.

In some implementations, the processing circuitry 608 receives, from the camera 622, image data representing a consumable (e.g., a container 1210, as described in conjunction with FIG. 12) for placement into the automated sample analyzer 600. The consumable may include one or more of: mixers (for replacement), an electrode (for replacement), a light source lamp (for replacement), a sample and/or reagent (for loading), and a rack or rack tray (for loading). The processing circuitry 608 classifies, using the image recognition engine 624 stored in the memory 610, the consumable into a class of consumables based on the image data. The class of consumables may include one or more of: mixer, electrode, light source lamp, sample, reagent, and the like. The image recognition engine 624 may operate using artificial intelligence and/or machine learning techniques, for example, as shown in FIGS. 1-4. The processing circuitry 608 transmits a control signal to physically adjust the sample input device 602 to receive the consumable. The control signal corresponds to the class of consumables. Physically adjusting the sample input device 602 may include providing access to a receptacle of the sample input device 602, for example, by opening a door/access panel 603.

In some implementations, the processing circuitry 608 transmits, to the display device 606, a display signal for displaying a visual representation of the class of consumables or a portion of the image data. In some implementations, the processing circuitry 608 transmits, to the display device 606, a display signal for displaying at least a portion of the image data.

FIG. 7 is a flow chart illustrating an example method 700 for updating the user data repository 620, in accordance with some implementations. The method 700 may be implemented by the processing circuitry 608 when executing the configuration control engine 614.

At operation 710, the processing circuitry 608 identifies an accessing user of the automated sample analyzer 600 and, upon validation, establishes the accessing user as the current user. The validation may include one or more of: facial recognition, fingerprint recognition, user identifier and password validation, voice recognition, and multi-factor authentication. The learning engine 616 may compare a current validation input and a prior validation input and, upon the current validation input being authenticated, automatically calibrate validation criteria with the current validation input.

At operation 720, the processing circuitry 608 receives at least a portion of the user-dependent configuration data from the user data repository 620 corresponding to the current user. The user-dependent configuration data may include access control data and/or usage model data. The access control data may include one or more of: authorization to adjudicate failures, authorization to perform maintenance of the automated sample analyzer, and authorization to configure the automated sample analyzer. The usage model data may include one or more of: a type of test run, a supply loading frequency, a number of times each workflow is performed, a language, and a preferred sequence of maintenance tasks (see, e.g., blocks 1302, 1304, 1306, and 1308 of FIG. 13).

At operation 730, the processing circuitry 608 amends the portion of the user-dependent configuration data from the user data repository 620 with new user-dependent configuration data when the new user-dependent configuration data is provided by the learning engine 616.

At operation 740, the processing circuitry 608 updates the user data repository 620 with the new user-dependent configuration data.

FIG. 8 is a flow chart illustrating an example method 800 for identifying and storing a pattern of interaction, in accordance with some implementations. The method 800 may be implemented by the processing circuitry 608 when executing the learning engine 616.

At operation 810, the processing circuitry 608 monitors interactions between the current user and the GUI.

At operation 820, the processing circuitry 608 evaluates the interactions to identify at least one pattern of interaction of the current user with the GUI. The pattern of interaction may be based, at least in part, on an amount of time the current user spent working at the automated sample analyzer. The pattern of interaction may be based, at least in part, on a usage frequency of the automated sample analyzer by the current user. The usage frequency may be indicated by color (e.g., color coded) on the GUI. For example, menu items may be color coded to indicate which tasks have been completed.

At operation 830, the processing circuitry 608 transforms the pattern of interaction into a format compatible with the portion of the user-dependent configuration data of the user data repository 620.

At operation 840, the processing circuitry 608 provides the pattern of interaction to the configuration control engine 614 in the compatible format.

In some implementations, the automated sample analyzer 600 includes a network connection configured to access an external data repository. At least a portion of the user data repository 620 is stored in the external data repository.

In some implementations, the configuration control engine 614 is configured to establish the accessing user as a new user and register the new user in the user data repository 620. Alternatively, the accessing user may be one of a plurality of registered users, who are already registered in the user data repository 620.

In some implementations, the learning engine 616 records the prior menu item usage of the current user in a log. The log is used to generate the user-dependent configuration data, for example, by analyzing statistical high frequency on specific functions, operators, times, shifts, days of the week, and the like. An artificial intelligence engine may analyze the prior menu item usage of the automated sample analyzer by the current user to generate the user-dependent configuration data.

In some implementations, the configuration control engine 614 causes the processing circuitry 608 to provide, via the GUI, a representation of most probable next action(s) of the user based on historical usage information of the user (or other users) stored in the user data repository 620. The configuration control engine 614 may cause the processing circuitry 608 to provide, to the current user via the GUI, a representation of a shortcut of sequential actions to an end goal predicted (e.g., using artificial intelligence or machine learning technology as shown in FIGS. 1-4). The configuration control engine 614 may cause the processing circuitry 608 to provide, to the current user via the GUI, a representation of a shortened workflow. The shortened workflow is selected based on an experience level of the current user identified by the learning engine 616. The configuration control engine 614 may cause the processing circuitry 608 to provide, via the GUI, a representation of a shortened workflow, the shortened workflow being selected based on at least one previous menu item selection of the current user identified by the learning engine 616. For example, certain menu items may be bolded or highlighted, as shown, for example, in FIG. 9. The representations may be provided by playing audio via a speaker controlled by the user interface engine.

The automated sample analyzer 600 may display the most (or top n frequent, where n is a positive integer, e.g., 50) patterns or a menu of interaction within the same time window. Then, upon user selection (e.g., click), the shortcut may be displayed.

Figure 9:
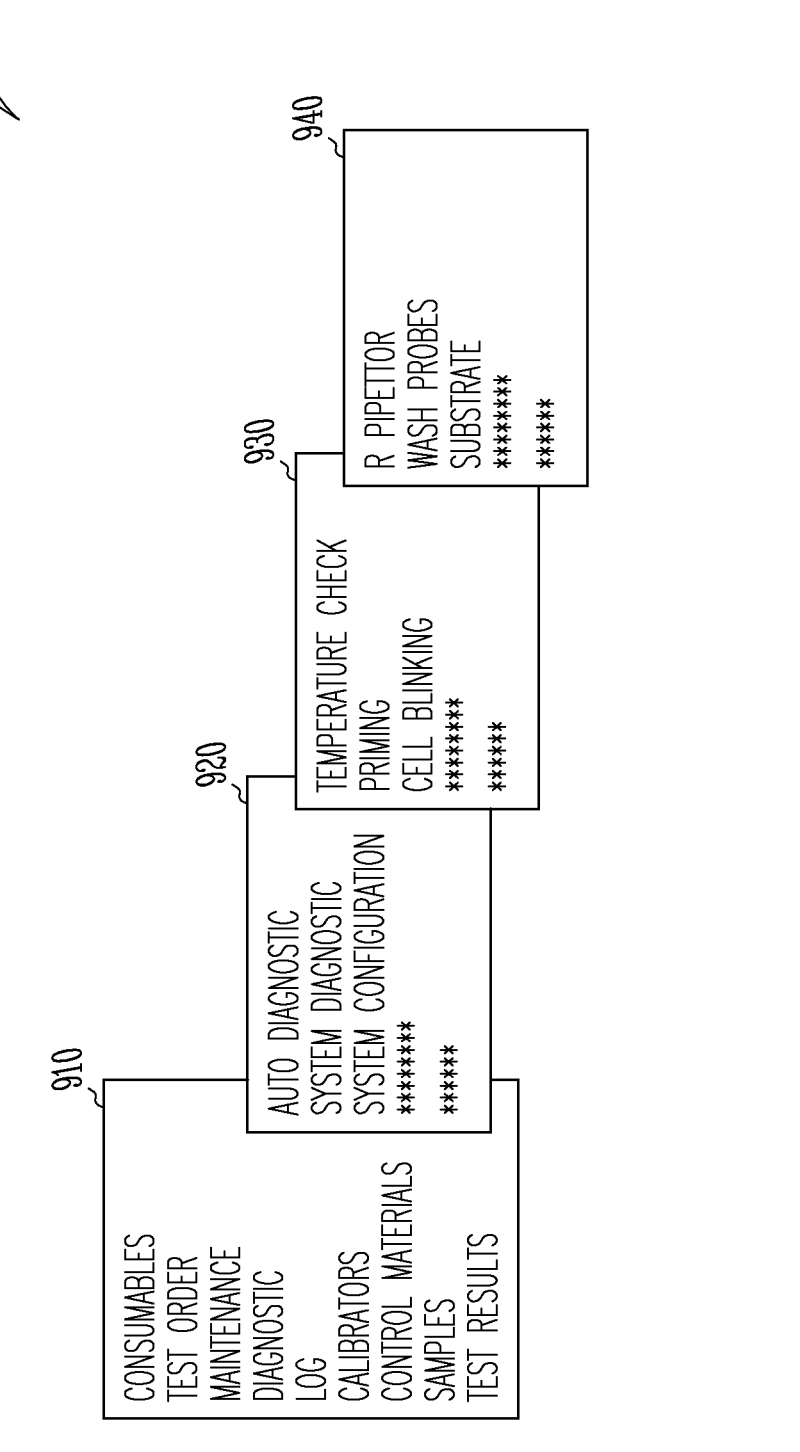
FIG. 9 illustrates an example menu, in accordance with some implementations.

FIG. 9 illustrates an example menu 900, in accordance with some implementations. The menu 900 may be presented at the display device 606 of the automated sample analyzer 600 and may be controlled using a touch screen (e.g., of the display device 606) or a mouse, keyboard, joystick, and the like coupled to the automated sample analyzer 600. As shown, the menu 900 includes sub-menus 910, 920, 930, and 940. The sub-menu 910 is presented initially. When the user selects "Diagnostic," the sub-menu 920 is shown. When the user selects "System Diagnostic," the sub-menu 930 is shown. When the user selects "Priming," the sub-menu 940 is shown. The menu items "Diagnostic," "System Diagnostic," "Priming," and "Substrate," are printed in bold because they are most commonly selected by the current user. This allows the current user to more easily cause the automated sample analyzer 600 to do the tasks the current user frequently requests or is likely to request.

In some implementations, after the user completes a current action, the GUI changes a color of the current action (e.g., in the menu) upon completion. The menu items representing actions in the menu may be color coded to indicate a frequency of the current user taking the actions.

According to some schemes, all users follow a same workflow to review details of different elements of the automated sample analyzer 600 via the display device 606. If a user is sufficiently trained or experienced with the automated sample analyzer 600, she might desire to bypass parts of this workflow, and might desire to view shorter paths, through the menu, to tasks she does frequently or is likely to do at a given time (e.g., 9 am on Monday morning).

According to some schemes, a menu hierarchy helps users locate functionality by separating menu items into different sub-menus. An experienced user may know the specific menu item she is seeking and might not need the menu hierarchy to locate the appropriate item.

Figure 10:
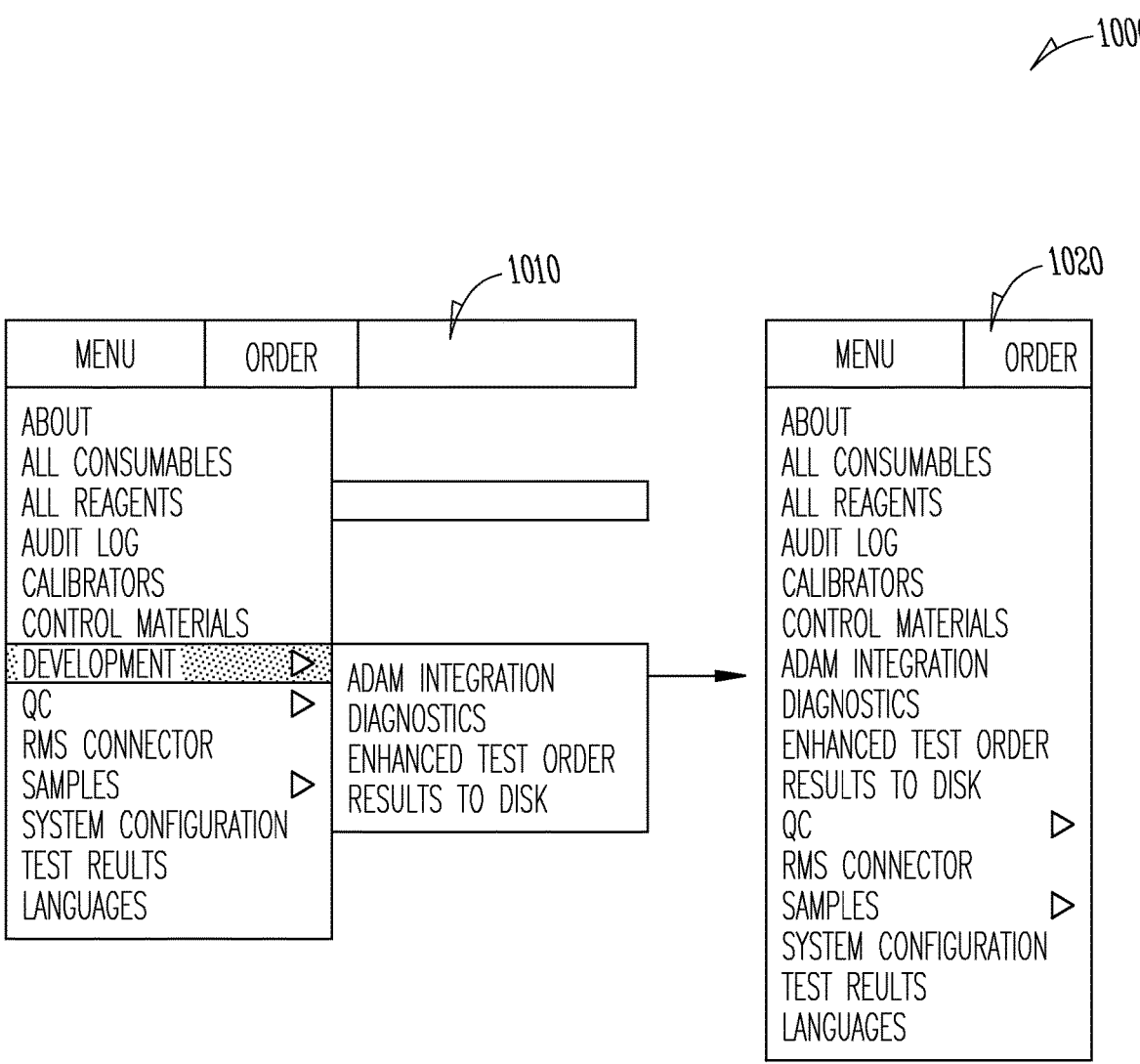
FIG. 10 illustrates an example collapsed menu hierarchy, in accordance with some implementations.

FIG. 10 illustrates an example collapsed menu hierarchy 1000, in accordance with some implementations. As shown, the menu 1010 may be collapsed into the menu 1020.

Some implementations recognize users using facial recognition technology (e.g., artificial intelligence or machine learning engine(s) as described in conjunction with FIGS. 1-4). Some implementations monitor all of a user's activities at the automated sample analyzer over a past time period (e.g., past 30 days). Some implementations rank user activities based on day of the week, hour of the day, etc., and adjust the GUI accordingly.

Figure 11A:
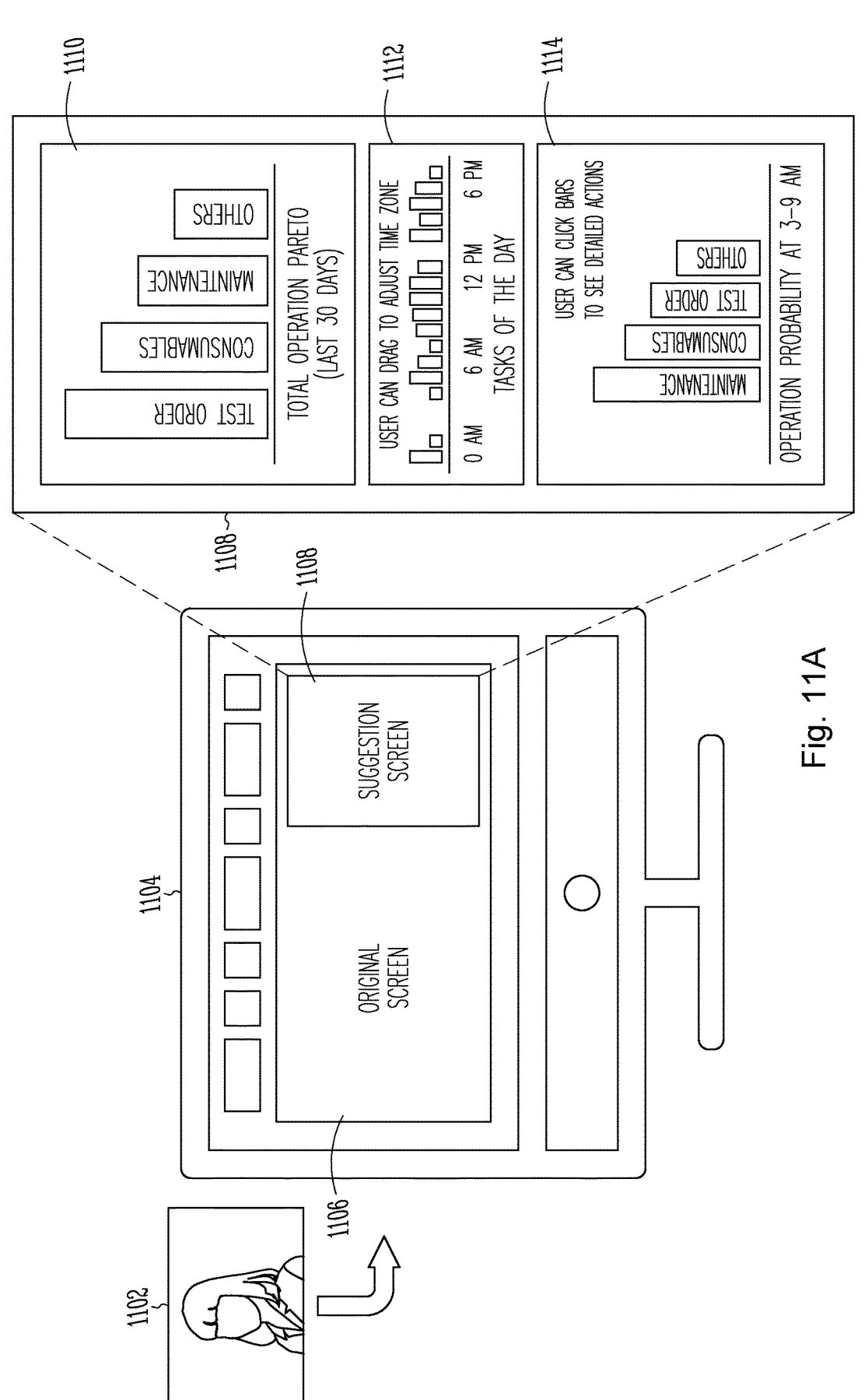
FIGS. 11A-11C illustrate example display data associated with an automated sample analyzer, in accordance with some implementations.
Figure 11B:
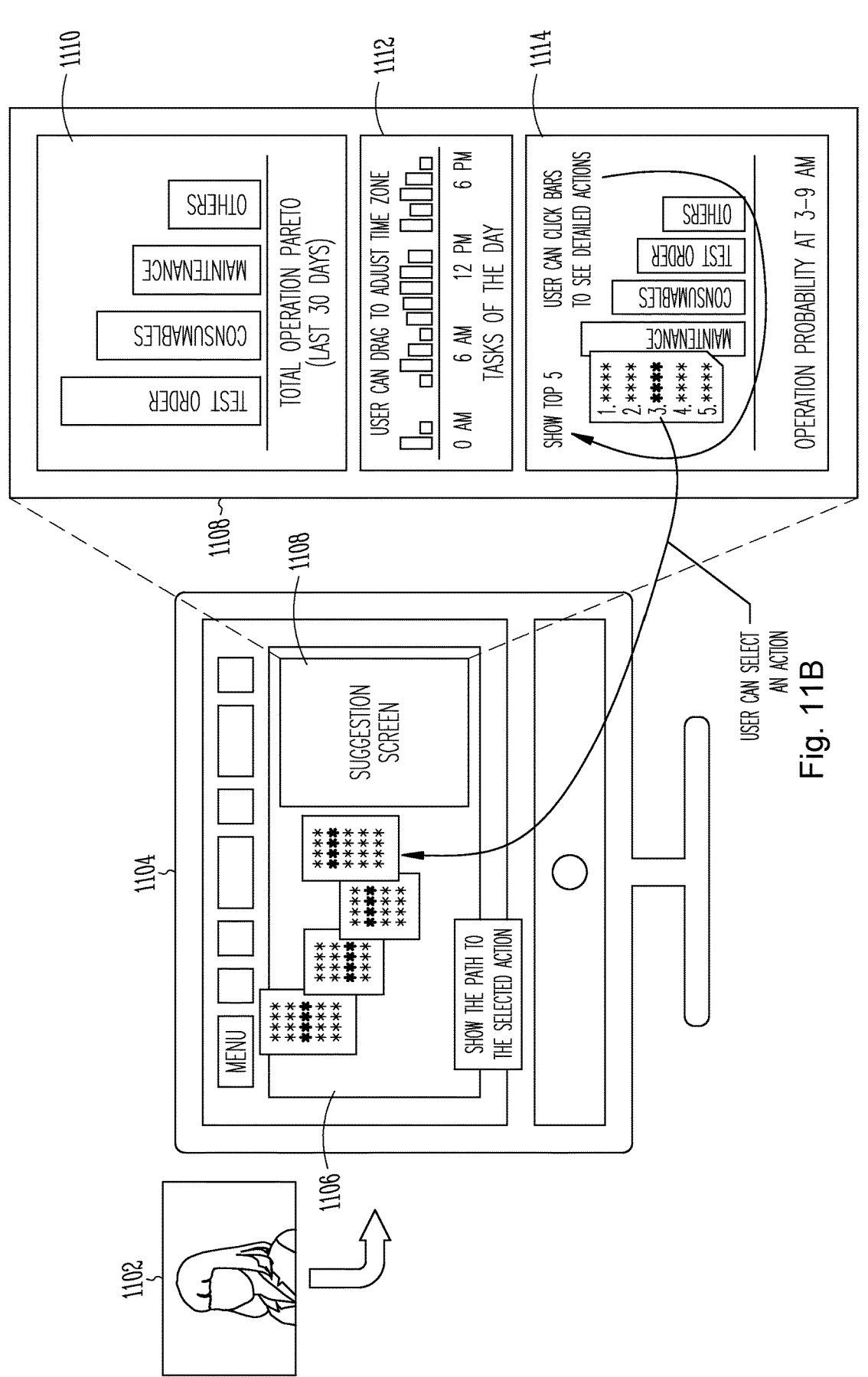
Figure 11C:
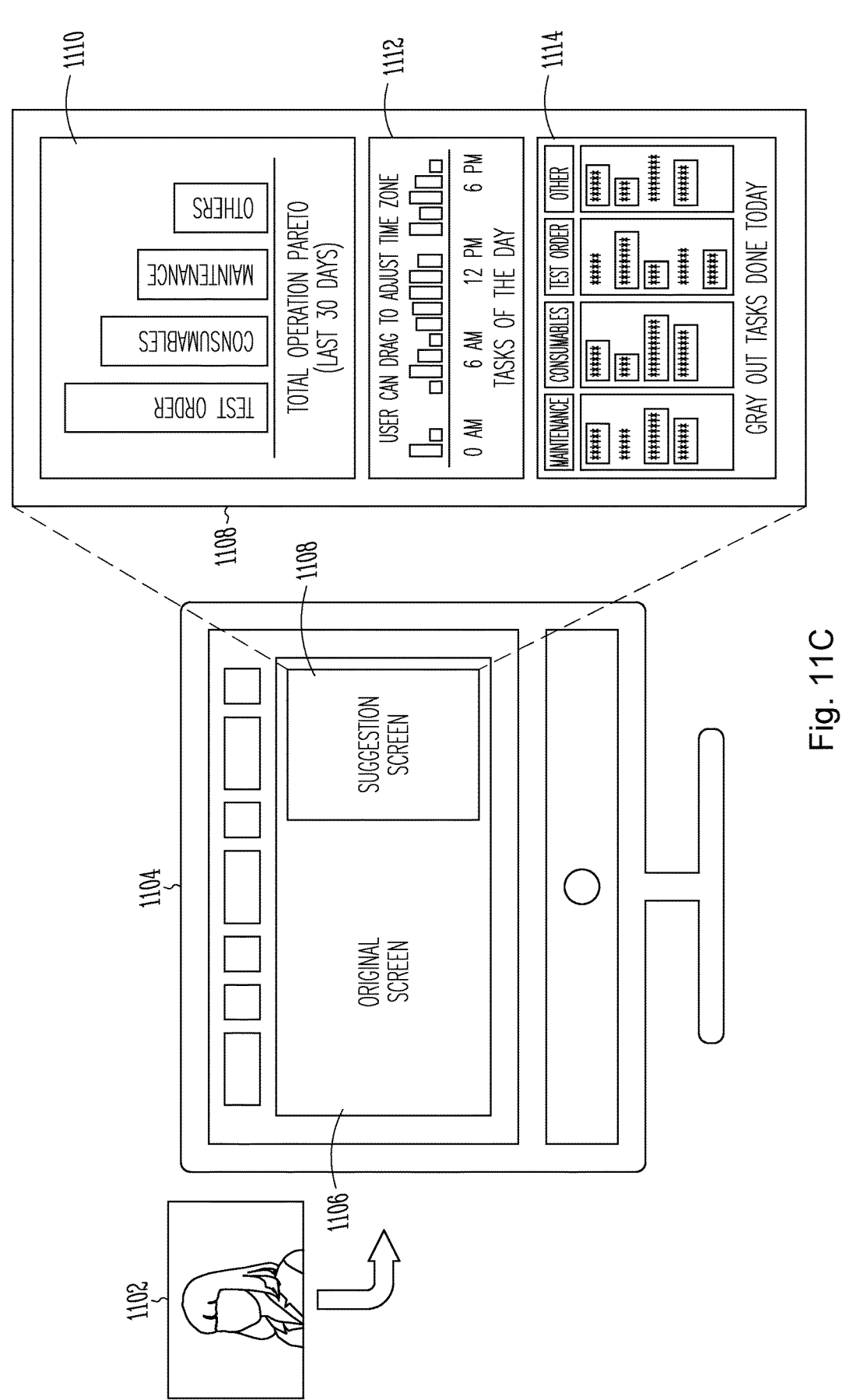

FIGS. 11A-11C illustrate example display data associated with an automated sample analyzer, in accordance with some implementations.

As shown in FIG. 11A, a user 1102 is identified (e.g., using facial recognition). In response, the display device 1104 is divided into at least original screen data 1106 and suggestion screen data 1108. The suggestion screen data 1108 includes total operation pareto 1110 for the last 30 days (or other time period), operations segregated by time 1112, and operation probability in each time block 1114. The user can drag the operations segregated by time 1112 to adjust the time block for the operation probability in each time block 1114. Artificial intelligence techniques (e.g., as shown in FIGS. 1-4) may be used to identify the actions suggested in the suggestion screen data 1108.

FIG. 11B differs from FIG. 11A because the original screen data 1106 shows a path to a selected action. The selected action is selected from the operation probability in each time block 1114, which may show the top five (or other number of) actions. The user may select one of those top five actions as the selected action the path for which is shown in the original screen data 1106. The original screen data 1106 may now include a shortcut for the selected task.

FIG. 11C differs from FIG. 11A because the operation probability in each time block 1114 greys out tasks that have been done today (or within another time period). The suggestion screen data 1108 may highlight tasks that have previously been done frequently and/or task that have not been done yet today (or during another time period).

Figure 12:
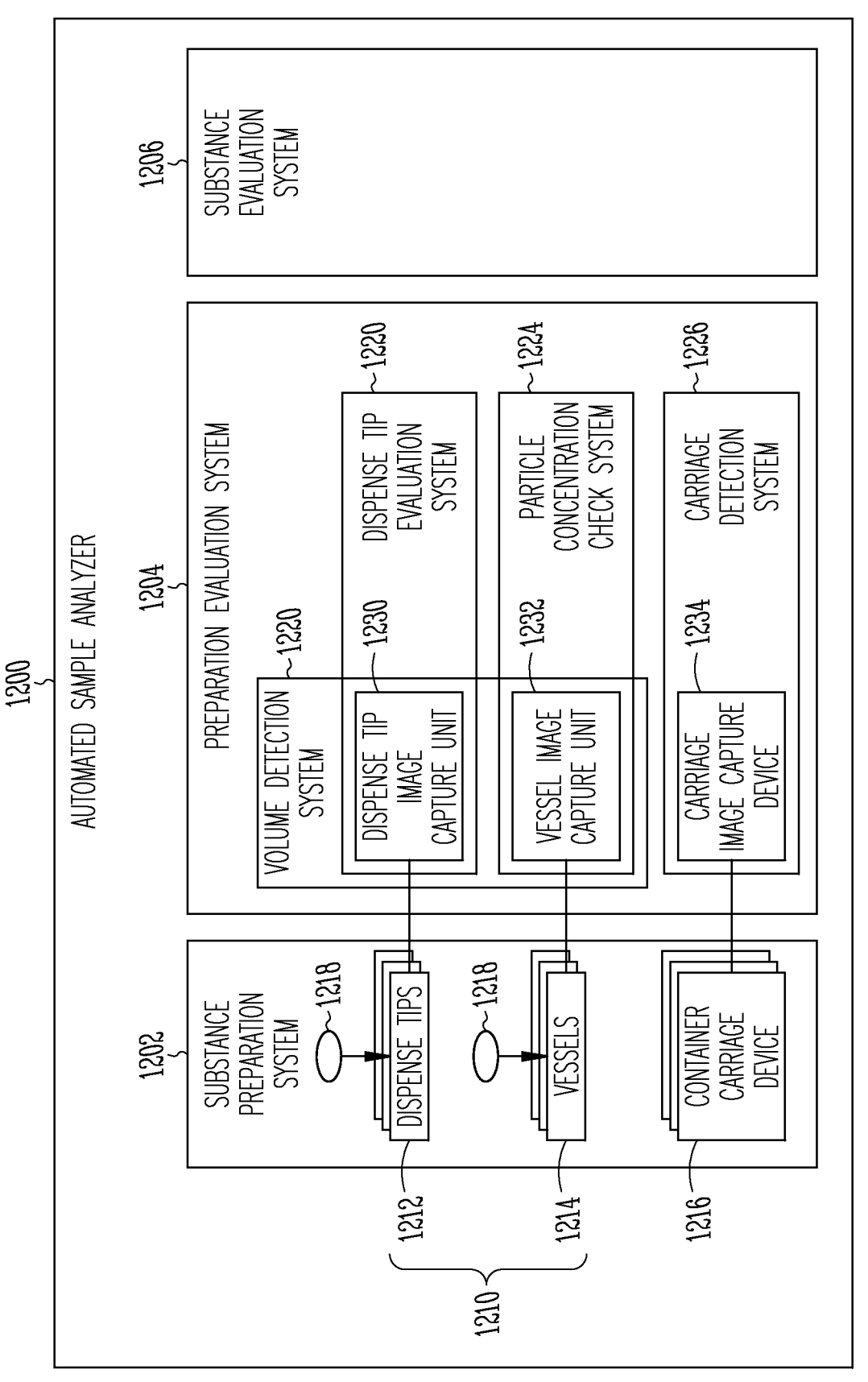
FIG. 12 is a block diagram of an example automated sample analyzer for analyzing a specimen, in accordance with some implementations.

FIG. 12 is a block diagram of an example automated sample analyzer 1200 for analyzing a biological (or other) specimen, in accordance with some implementations. In some implementations, the automated sample analyzer 1200 includes a substance preparation system 1202, a preparation evaluation system 1204, and a substance evaluation system 1206. One or more containers 1210 are used with the systems of the automated sample analyzer 1200 and include dispense tips 1212 and vessels 1214. Also shown are one or more container carriage devices 1216 that are provided in the instrument 1200. Further, the preparation evaluation system 1204 includes a volume detection system 1220, a dispense tip evaluation system 1222, and a carriage detection system 1226. In some implementations, the volume detection system 1220 utilizes a dispense tip image capture unit 1230 and a vessel image capture unit 1232. In some implementations, the dispense tip evaluation system 1222 uses the dispense tip image capture unit 1230, and the particle concentration check system 1224 uses the vessel image capture unit 1232. In some implementations, the carriage detection system 1226 uses a carriage image capture unit 1234.

The automated sample analyzer 1200 operates to analyze a biological specimen for various purposes. In some implementations, the automated sample analyzer 1200 is configured to analyze a blood sample and operates to collect, test, process, store, and/or transfuse blood and its components.

The substance preparation system 1202 operates to prepare one or more substances for further analysis by the substance evaluation system 1206. In some implementations, the substance preparation system 1202 operates to aliquot substances 1218 with containers 1210, aspirate substances 1218 from containers 1210 and dispense substances 1218 to containers 1210.

The preparation evaluation system 1204 operates to evaluate the preparation of substances for subsequent analysis by the substance evaluation system 1206. In some implementations, the preparation evaluation system 1204 utilizes one or more image capture units to determine whether substances 1218 have been appropriately prepared for analysis. As described herein, the preparation evaluation system 1204 provides direct and simple measurements of volume or integrity of a substance 1218 to determine whether the substance 1218 is appropriately prepared so that the substance evaluation system 1206 produces a reliable result using the substance 1218.

The substance evaluation system 1206 operates to evaluate the substance 1218 that is prepared by the substance preparation system 1202.

Figure 13:
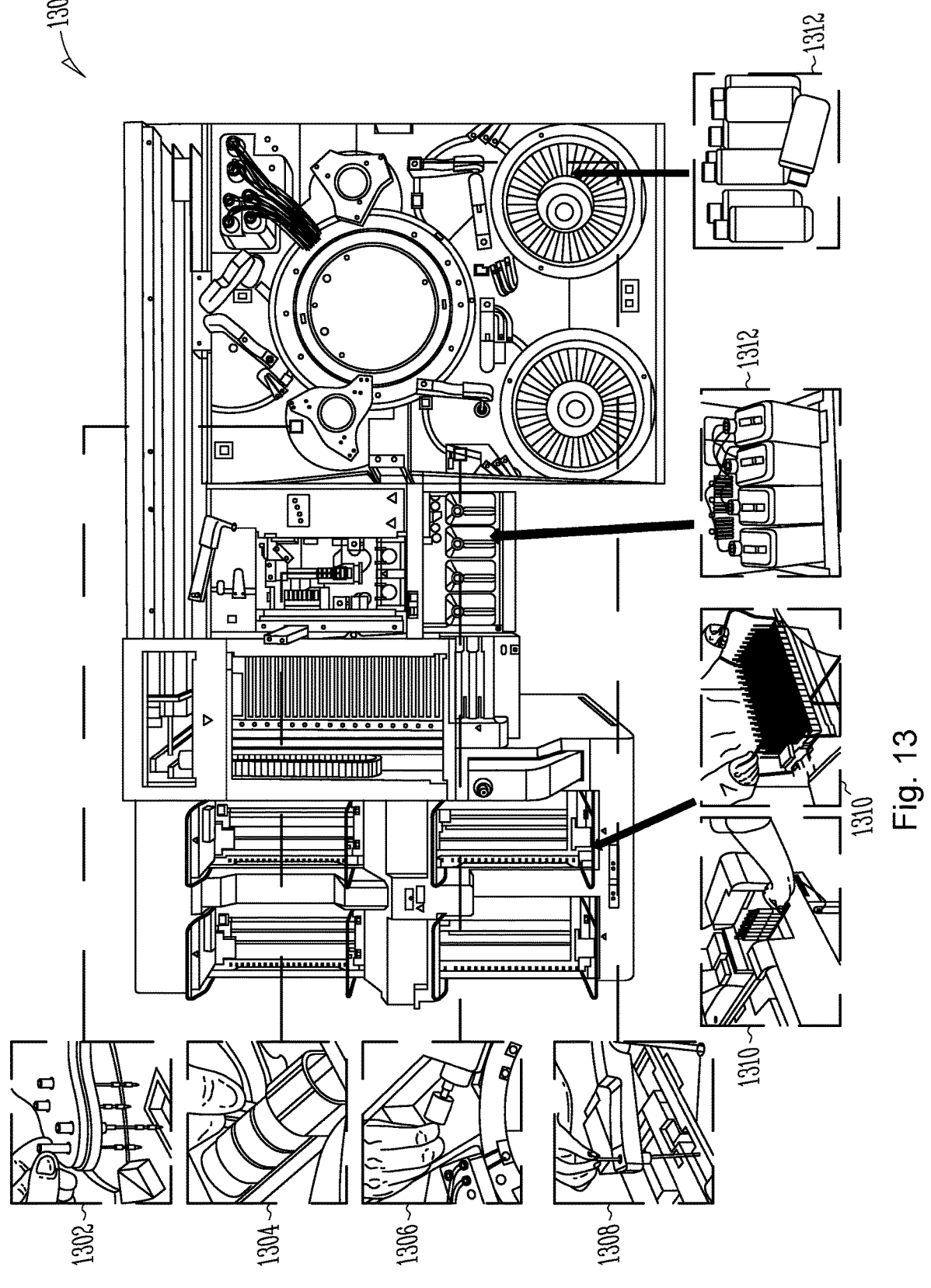
FIG. 13 illustrates an example automated sample analyzer, in accordance with some implementations.

FIG. 13 illustrates an example automated sample analyzer 1300, in accordance with some implementations. In some implementations, a user may be holding a container 1210 (e.g., a consumable) for insertion into the automated sample analyzer 1300 (e.g., into the sample input device 602).

In some cases, the user may wish to replace/clean up parts of the automated sample analyzer 1300 during maintenance thereof. Examples of this include replacing mixers 1302, replacing the electrode 1304, replacing the light source lamp 1306, and replacing the sample and reagent 1308. In some cases, the user may wish to load samples with a rack or a rack tray 1310. In some cases, the user may load reagents 1312.

Figure 14:
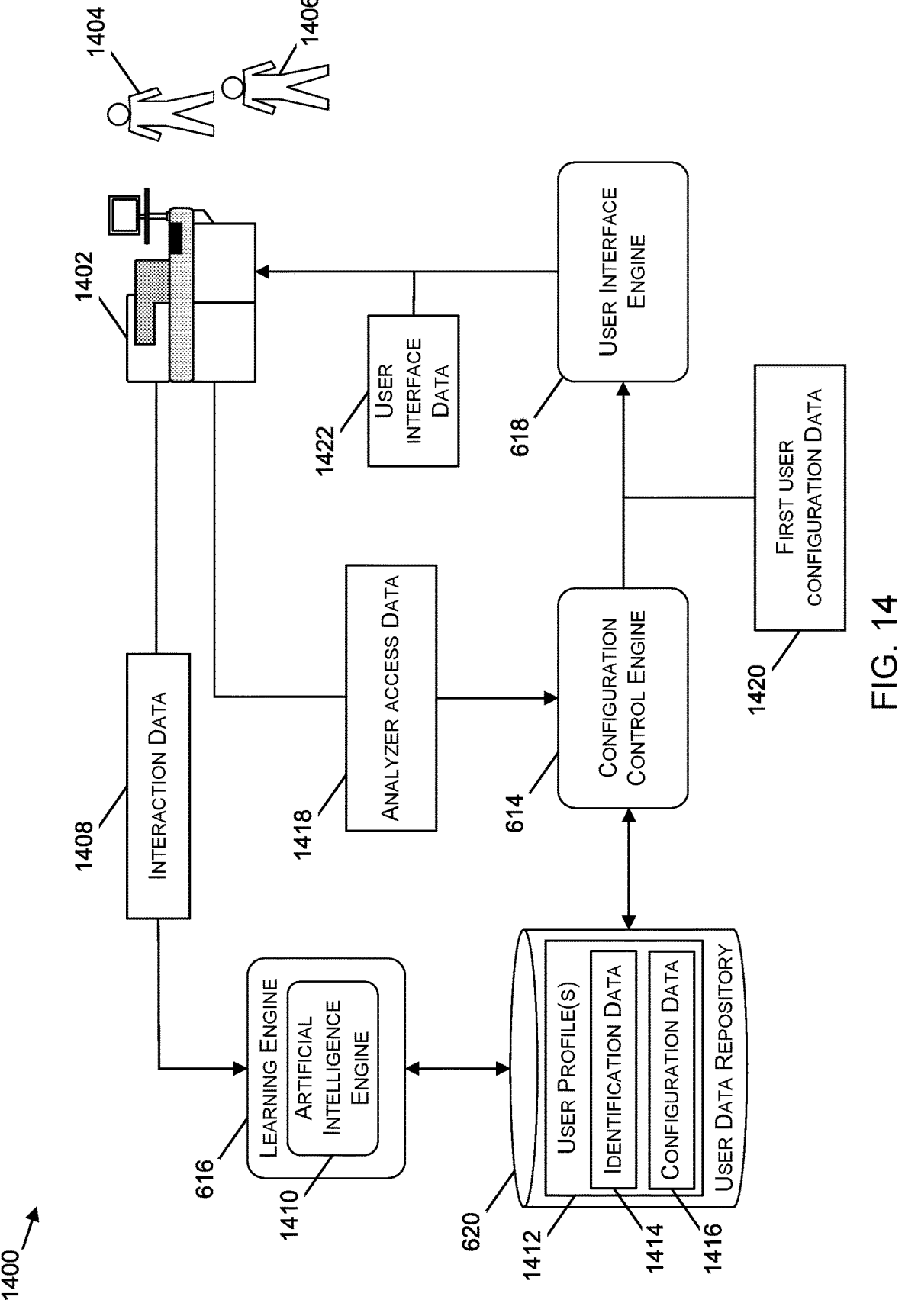
FIG. 14 illustrates an example system to configure automated sample analyzers based on configuration data derived from patterns of interaction by users of the automated sample analyzers, in accordance with some implementations.

FIG. 14 illustrates an example system 1400 to configure automated sample analyzers based on configuration data derived from patterns of interaction by users of the automated sample analyzers, in accordance with some implementations. The system 1400 can include an automated sample analyzer 1402. The automated sample analyzer 1402 can be operated by a number of users, such as a first user 1404 and a second user 1406. In one or more examples, at least a portion of the users of the automated sample analyzer 1402 can operate the automated sample analyzer 1402 for different purposes. In one or more additional examples, at least a portion of the users of the automated sample analyzer 1402 can operate the automated sample analyzer 1402 for the same purpose.

In one or more illustrative examples, a first portion of users of the automated sample analyzer 1402 can operate the automated sample analyzer 1402 to perform maintenance on the automated sample analyzer 1402. In one or more additional illustrative examples, a second portion of users of the automated sample analyzer 1402 can operate the automated sample analyzer 1402 to analyze samples provided to the automated sample analyzer 1402. In one or more further illustrative examples, other users of the automated sample analyzer 1402 can operate the automated sample analyzer 1402 to perform diagnostic operations or calibration operations with respect to the automated sample analyzer 1402. In still other illustrative examples, additional users of the automated sample analyzer 1402 can operate the automated sample analyzer 1402 to obtain information stored by the automated sample analyzer 1402, such as test results or operations logs.

The automated sample analyzer 1402 can monitor interactions by the users 1404, 1406 with the automated sample analyzer 1402. Monitoring interactions with the automated sample analyzer 1402 can include identifying user interfaces accessed during operation of the automated sample analyzer 1402 by the first user 1404 and the second user 1406. Monitoring interactions with the automated sample analyzer 1402 can also include identifying menus accessed during operation of the automated sample analyzer 1402 by the first user 1404 and the second user 1406. Additionally, monitoring interactions with the automated sample analyzer 1402 can include determining selections of user interface elements or user interface items included in user interfaces displayed by the automated sample analyzer 1402. As used herein, a user interface element or a user interface item can correspond to a portion of a user interface that is selectable to cause the automated sample analyzer 1402 to perform an action. The action can include at least one of displaying information, navigating to another user interface, or causing a component of the automated sample analyzer 1402 to perform an operation, such as causing an access panel to open or close or causing a sample to be analyzed. In one or more illustrative examples, user interface elements can include tabs, fields, radio boxes, toolbars, drop down menus, buttons, toggles, one or more combinations thereof, and the like. In one or more additional illustrative examples, the automated sample analyzer 1402 can monitor times, days, and so forth of interactions by users of the automated sample analyzer 1402.

In various examples, interactions by users with the automated sample analyzer 1402 can be captured by cameras of the automated sample analyzer 1402. In this way, the automated sample analyzer 1402 can generate image data that indicates interactions of users with the automated sample analyzer 1402. For example, the automated sample analyzer 1402 can capture images of samples provided to the automated sample analyzer 1402 by users. In one or more examples, the images can include labels on containers that include the samples being analyzed by the automated sample analyzer 1402. The labels can include information about the samples. The images can also indicate characteristics of the samples, such as color, shape, transparency, one or more combinations thereof, and the like. Images captured by the automated sample analyzer 1402 can also show users accessing, moving, or otherwise interacting with physical components of the automated sample analyzer 1402. To illustrate, images captured by the automated sample analyzer 1402 can show users opening an access panel or placing samples into a chamber of the automated sample analyzer 1402.

The automated sample analyzer 1402 can generate interaction data 1408 based on interactions with the automated sample analyzer 1402 and send the interaction data 1408 to the learning engine 616. The interaction data 1408 can correspond to data collected by the automated sample analyzer 1402 related to interactions by users with the automated sample analyzer 1402. In one or more examples, the learning engine 616 can include an artificial intelligence engine 1410 that analyzes the interaction data 1408 to find correlations, patterns, and/or other relationships between portions of the interaction data 1408. The interaction data 1408 can include selections of user interface elements, navigating to one or more user interfaces, input provided via one or more menus, opening or closing access panels of the automated sample analyzer 1402, or other actions performed with respect to the automated sample analyzer 1402. The interaction data 1408 can be captured by one or more input devices of the automated sample analyzer 1402. In various examples, the artificial intelligence engine 1410 can analyze the interaction data 1408 to generate user models for users of the automated sample analyzer 1402.

Additionally, the learning engine 616 can be coupled to or otherwise access a user data repository 620. The user data repository 620 can store user profiles 1412. The user profiles 1412 can include information about users of the automated sample analyzer 1402. In one or more examples, the user profiles 1412 can include identification data 1414. The identification data 1414 can be used to verify an identity of users requesting access to the automated sample analyzer 1402 and enable the users to access the automated sample analyzer 1402 in response to verification of the identity of the users. The configuration data 1416 can indicate one or more configurations of the automated sample analyzer 1402 that correspond to a user of the automated sample analyzer 1402. The configuration data 1416 can be provided to the automated sample analyzer 1402 in response to a user accessing the automated sample analyzer 1402, such as via an authentication process using the identification data 1414.

The artificial intelligence engine 1410 can analyze the interaction data 1408 to determine patterns of interactions of individuals users with the automated sample analyzer 1402. In one or more examples, the artificial intelligence engine 1410 can analyze the portions of the interaction data 1408 that correspond to the first user 1404 to determine interactions of the first user 1404 with the automated sample analyzer 1402. In various examples, the artificial intelligence engine 1410 can determine that interactions with the automated sample analyzer 1402 correspond to the first user 1404 by analyzing the interaction data 1408 with respect to an identifier of the first user 1404, such as an employee identification number. In one or more illustrative examples, when the first user 1404 initiates a session with the automated sample analyzer 1402 using an authentication procedure, the identifier of the first user 1404 can be associated with the interactions of the first user 1404 with the automated sample analyzer 1402. In one or more additional examples, the artificial intelligence engine 1410 can determine an identity of the first user 1404 and actions performed by the first user 1404 based on image data captured by one or more cameras of the automated sample analyzer 1402. In this way, the artificial intelligence engine 1410 can determine interactions that correspond to the first user 1404 that are included in the interaction data 1408. As a result, the actions performed by the first user 1404 with respect to a session of use of the automated sample analyzer 1402 can be tracked.

The artificial intelligence engine 1410 can determine patterns of interaction of the first user 1404 with the automated sample analyzer 1402 by identifying correlations between inputs provided by the first user 1404 at the automated sample analyzer 1402. For example, the artificial intelligence engine 1410 can determine one or more sequences of inputs made by the first user 1404 using the automated sample analyzer 1402. The sequences of inputs can correspond to a series of user interfaces accessed by the first user 1404 and/or a series of user interface element selections by the first user 1404 at the automated sample analyzer 1402. In at least some examples, the artificial intelligence engine 1410 can determine that a pattern of interactions of the first user 1404 corresponds to a period of time, such as a window of time during the workday of the first user 1404. For example, the period of time can include at least one of a time or date at which an action was performed. The period of time can also correspond to a shift in which an action was performed. In various examples, the artificial intelligence engine 1410 can determine a first pattern of interaction by the first user 1404 during a first time period of the workday of the first user 1404 and a second pattern of interaction by the first user 1404 during a second time period of the workday of the first user 1404. In one or more illustrative examples, the first pattern of interactions can correspond to accessing a series of user interfaces and providing a sample to a chamber of the automated sample analyzer 1402 and the second pattern of interactions can correspond to accessing an additional series of user interfaces to generate a report using data stored by or otherwise accessible to the automated sample analyzer 1402. In one or more examples, the pattern of interactions of the first user 1404 can include a chronological series of inputs provided to the automated sample analyzer 1402 to generate the report.

In one or more examples, the artificial intelligence engine 1410 can determine patterns of interaction with respect to classes of users of the automated sample analyzer 1402. For example, the artificial intelligence engine 1410 can determine users of the automated sample analyzer 1402 that have a same or similar title, that have a same supervisor, that have same or similar job duties, or that are otherwise related within an organization to determine a class of individuals. In various examples, the artificial intelligence engine 1410 can determine a title, supervisor, or job duties of users by accessing information stored in the user profiles 1412. In one or more additional examples, the artificial intelligence engine 1410 can determine a class of individuals by identifying users of the automated sample analyzer 1402 that have a same or similar pattern of interaction with the automated sample analyzer 1402. The artificial intelligence engine 1410 can also determine that individuals have a same or similar pattern of interaction with the automated sample analyzer 1402 by identifying individuals that perform at least a threshold percentage of interactions that are the same with respect to the automated sample analyzer 1402. Additionally, the artificial intelligence engine 1410 can determine individuals that have a same or similar pattern of interaction by identifying individuals that perform a sequence of interactions that have at least at threshold number of common interactions. After determining a number of users of the automated sample analyzer 1402 that can be included in a same class, the artificial intelligence engine 1410 can analyze the interaction data 1408 with respect to users of the automated sample analyzer 1402 to determine one or more patterns of interaction performed by users of the automated sample analyzer 1402 that are included in the class. In one or more illustrative example, the interactions used to determine users included in a same class can be different from interactions used to determine a configuration of the automated sample analyzer 1402 for the class of users.

Patterns of interaction determined by the artificial intelligence engine 1410 with respect to individual users and/or classes of users of the automated sample analyzer 1402 can be used by the artificial intelligence engine 1410 to determine configuration data 1416 for the individual users and/or classes of users of the automated sample analyzer 1402. The configuration data 1416 can indicate a series of user interfaces that are accessible to a user associated with the configuration data. The configuration data 1416 can also indicate a layout, appearance, or functionality of one or more user interface elements included in the user interfaces that are accessible to the users associated with the configuration data 1416. In one or more additional examples, the configuration data 1416 can indicate a shortcut that can be displayed in a user interface in order to access one or more additional user interfaces that are frequently accessed by one or more users of the automated sample analyzer 1402.

In one or more illustrative examples, the configuration data 1416 can indicate a navigation path through a number of user interfaces. In one or more examples, the navigation path can be indicated in the number of user interfaces by highlighting user interface elements that correspond to the navigation path. For example, a navigation path to analyze a sample using the automated sample analyzer 1402 can include a first user interface, a second user interface, and a third user interface. The first user interface can include a first plurality of user interface elements that are selectable to navigate to a first number of additional user interfaces and the second user interface can include a second plurality of user interface elements that are selectable to navigate to a second number of additional user interfaces. In this scenario, the configuration data 1416 can highlight a user interface element of the first plurality of user interface elements that is selectable to navigate to the second user interface and highlight a user interface element of the second plurality of user interface elements that is selectable to navigate to the third user interface. In this way, the amount of time and resources utilized by the user to navigate to the third user interface are minimized. In various examples, the user interface elements associated with the navigation path can be highlighted by bolding words and/or symbols associated with the user interface elements, causing the user interface elements to have different characteristics, such as color, shape, etc., in relation to characteristics of other user interface elements, or a combination thereof. In one or more additional examples, the first user interface can include a single user interface element that is selectable to navigate to the second user interface, such as a "Next" button, and the second user interface can include a single user interface element to navigate to the third user interface.

In one or more examples, the artificial intelligence engine 1410 can implement one or more machine learning techniques to identify one or more patterns of interaction and/or configurations for users of the automated sample analyzer 1402. In one or more illustrative examples, the artificial intelligence engine 1410 can implement one or more neural networks that analyze the portions of the interaction data 1408 to determine patterns of interaction and configurations for users of the automated sample analyzer 1402. The artificial intelligence engine 1410 can also implement one or more machine learning techniques to determine patterns of interaction by users of the automated sample analyzer 1402 and/or determine configurations for the users of the automated sample analyzer 1402. To illustrate, interaction data that includes input provided by a given user via one or more menus of the automated sample analyzer 1402 during a number of sessions and/or input captured by at least one of a camera of the automated sample analyzer 1402 can be provided as input data to a trained model of the artificial intelligence engine 1410. The artificial intelligence engine 1410 can then generate a configuration of the automated sample analyzer 1402 for the given user using the trained model. In one or more illustrative examples, the configuration can include at least one of a series of menus that can be accessible to the given user during a session of the automated sample analyzer 1402, a layout of one or more user interfaces displayed by the automated sample analyzer 1402 during a session, or a shortcut available to the given user during a session of the automated sample analyzer 1402. The machine learning techniques implemented by the artificial intelligence engine 1410 can analyze a large volume of data obtained by the automated sample analyzer 1402 in order to provide accurate predictions with regard to interactions of users with the automated sample analyzer 1402. In this way, the artificial intelligence engine 1410 can generate configurations for large numbers of users of the automated sample analyzer 1402 that accurately correspond to interactions of the users with the automated sample analyzer 1402 and provide a customized, streamlined experience for the users with the automated sample analyzer 1402.

Additionally, the artificial intelligence engine 1410 can implement one or more machine learning techniques with respect to the automated sample analyzer 1402 in order to analyze image data captured by the automated sample analyzer 1402. In one or more examples, the artificial intelligence engine 1410 can implement one or more machine learning techniques to perform facial recognition to enable users of the automated sample analyzer 1402 to access the automated sample analyzer 1402. Further, the artificial intelligence engine 1410 can use one or more machine learning techniques to analyze images obtained by the automated sample analyzer 1402 that correspond to interactions of users with the automated sample analyzer 1402 to determine patterns of interaction with the automated sample analyzer 1402. For example, the artificial intelligence engine 1410 can implement one or more machine learning techniques to analyze images obtained from the automated sample analyzer 1402 to determine that a pattern of interaction of the first user 1404 with the automated sample analyzer 1402 includes placing a sample in a chamber of the automated sample analyzer 1402 or opening an access panel to perform maintenance on the automated sample analyzer 1402.

In one or more illustrative examples, the first user 1404 can request access to the automated sample analyzer 1402 by providing analyzer access data 1418. The analyzer access data 1418 can include at least one of one or more images of the user 1406, biometric data of the user 1406, or login credentials of the user 1406, such as a username and password. In response to receiving the analyzer access data 1418, the configuration control engine 614 can verify an identity of the user 1404 by analyzing the analyzer access data 1418 with respect to the identification data 1412 included in a user profile 1412 of the first user 1404. After authentication of the user 1404, the configuration control engine 614 can access configuration data 1416 included in the user profile 1412 of the first user 1404. The configuration control engine 614 can generate first user configuration data 1420 from the configuration data 1416 stored in the user profile 1412 of the first user 1404 and send the first user configuration data 1420 to the user interface engine 618. In one or more additional examples, the first user configuration data 1420 can be at least time-based. That is, the first user configuration data 1420 for the first user 1404 can indicate one or more user interfaces and/or layouts of user interfaces that are implemented at a specified period of time, such as at the beginning of a shift. In one or more further examples, the first user configuration data 1420 can be determined at least in part based on a role or class of the first user 1404. For example, the user profile 1412 of the first user 1404 can indicate that the first user 1404 is a supervisor, a maintenance worker, a calibration worker, a quality control worker, or one or more combinations thereof. In various examples, different configurations of the automated sample analyzer 1402 can be associated with supervisors, maintenance workers, calibration workers, and quality control workers.

The first user configuration data 1420 can include data that the user interface engine 618 can use to generate user interface data 1422. The user interface data 1422 can indicate a sequence in which to display one or more user interface via a display device of the automated sample analyzer 1402. The user interface data 1422 can also indicate a layout of user interface elements for individual user interfaces displayed via the automated sample analyzer 1402. Further, the user interface data 1422 can indicate a shortcut to display in one or more user interfaces that can directly cause the first user 1404 to one or more menus and/or user interfaces accessed by the first user 1404 and bypass other menus/user interfaces that are not accessed by the first user 1404. In this way, a customized and streamlined experience can be provided to the user 1402 during operation of the automated sample analyzer 1402. Additionally, the artificial intelligence engine 1410 can determine configurations and workflows that can be used to identify instances that occur when users deviate from specified configurations or workflows. As a result, the automated sample analyzer 1402 can alert a user when the user performs an operation that does not correspond to a given workflow or configuration. The automated sample analyzer 1402 can also determine one or more operations, menus, and/or user selections that can be performed to rectify the error and present one or more user interface elements that are selectable to re-implement the specified configuration or workflow.

In various examples, the artificial intelligence engine 1410 can also utilize one or more machine learning techniques to recognize images that correspond to an interaction included in a pattern of interactions and cause a subsequent action included in the pattern of interactions to take place. To illustrate, after analyzing images obtained by the automated sample analyzer 1402 to determine that the first user 1404 of the automated sample analyzer 1402 has placed a sample in the automated sample analyzer 1402 and closed an access panel, the automated sample analyzer 1402 can perform one or more operations involved in the analysis of the sample. Additionally, the artificial intelligence engine 1410 can also implement one or more machine learning techniques to analyze images of a sample to determine a type related to the sample, such as whether the sample includes whole blood or whether the sample includes plasma. In response to determining the type of the sample, the automated sample analyzer 1402 can perform operations related to analyzing the type of sample placed in the automated sample analyzer 1402.

Although the illustrative example of FIG. 14 includes a single automated sample analyzer 1402 and two users 1404, 1406, in additional implementations, the system 1400 can include multiple automated sample analyzers with each automated sample analyzer having multiple users. Additionally, the system 1400 can include automated sample analyzers located in a number of different organizations and/or located in a number of different locations. Further, in one or more implementations, at least a portion of the configuration control engine 614, the learning engine 616, the user interface engine 618, and/or the user data repository 620 can be located within the automated sample analyzer 1402. In one or more additional examples, at least a portion of the configuration control engine 614, the learning engine 616, the user interface engine 618, and/or the user data repository 620 can be implemented remotely from the automated sample analyzer 1402, such as being implemented in a cloud computing or other distributed architecture.

Some implementations may be described as numbered examples (Example 1, 2, 3, etc.). These numbered examples are provided as examples only and do not limit the disclosed technology.

Example 1 is an automated sample analyzer comprising: a sample input device receiving a liquid sample; a sample analyzing device reading measurements associated with the liquid sample; a display device displaying a graphical user interface (GUI) to a current user of the automated sample analyzer, the GUI being for controlling or maintaining the automated sample analyzer by the current user; processing circuitry; and a memory storing: a receiving engine which, when executed by the processing circuitry, receiving the measurements associated with the liquid sample from the sample analyzing device and storing the received measurements in memory; a configuration control engine which, when executed by the processing circuitry, causes the processing circuitry to set a configuration of a user model to correspond to the current user of the automated sample analyzer; a learning engine which, when executed by the processing circuitry, causes the processing circuitry to detect and collect at least one pattern of interaction of the current user with the GUI; and a user interface engine which, when executed by the processing circuitry, causes the processing circuitry to configure the GUI according to user-dependent configuration data of the configuration of the user model corresponding to the current user, the user-dependent configuration data being received from a user data repository; wherein the learning engine, when executed by the processing circuitry, causes the processing circuitry to: identify an accessing user and, upon validation, establish the accessing user as the current user; monitor interaction between the current user and the GUI and store interaction data of the current user in association with time; determine, based on the interaction data, at least one time-cyclical pattern of interaction between the current user and the GUI; and store the at least one time-cyclical pattern of interaction.

In Example 2, the subject matter of Example 1 includes, wherein the configuration control engine, when executed by the processing circuitry, causes the processing circuitry to: identify the accessing user and, upon validation, establish the accessing user as the current user; determine, based on a current time and the stored at least one time-cyclical pattern of interaction, a pattern of interaction for the current time; and display, within the GUI, a shortcut to implement the pattern of interaction for the current time.

In Example 3, the subject matter of Example 2 includes, wherein the configuration control engine, when executed by the processing circuitry, further causes the processing circuitry to: forgo displaying the shortcut in response to a user request.

In Example 4, the subject matter of Examples 2-3 includes, wherein the configuration control engine operates at asynchronously with the learning engine.

In Example 5, the subject matter of Examples 1-4 includes, wherein the user data repository comprises a database.

In Example 6, the subject matter of Examples 1-5 includes, a network connection configured to access an external data repository, wherein at least a portion of the user data repository is stored at the external data repository.

In Example 7, the subject matter of Examples 1-6 includes, wherein the configuration control engine is configured to: establish the accessing user as a new user, upon validation; and register the new user in the user data repository.

In Example 8, the subject matter of Examples 1-7 includes, wherein the accessing user is one of a plurality of registered users.

In Example 9, the subject matter of Examples 1-8 includes, wherein the user-dependent configuration data includes menu optimization data that defines a menu optimization comprising a set of menus for presentation within the GUI or a set of menu items for presentation within the menus of the GUI.

In Example 10, the subject matter of Example 9 includes, wherein the menu optimization data is derived from prior menu usage or prior menu item usage of the current user.

In Example 11, the subject matter of Example 10 includes, wherein the menu optimization data is derived by artificial intelligence menu usage review of the prior menu usage of the current user.

In Example 12, the subject matter of Example 11 includes, wherein an artificial intelligence engine analyzes a prior menu usage frequency of the current user to generate the user-dependent configuration data.

In Example 13, the subject matter of Examples 11-12 includes, wherein the menu optimization is implemented without prompting the current user to cause the menu optimization.

In Example 14, the subject matter of Examples 11-13 includes, displaying an optimized menu; receiving, via the GUI, a request to revert to a prior version of the menu; and responsive to the request, displaying the prior version of the menu.

In Example 15, the subject matter of Examples 10-14 includes, wherein the menu optimization is implemented in response to a user request for menu optimization.

In Example 16, the subject matter of Examples 1-15 includes, wherein the new user-dependent configuration data that is updated in the user data repository comprises different GUI configurations for different times with at least a first GUI configuration for a first time range and a second GUI configuration for a second time range.

In Example 17, the subject matter of Example 16 includes, wherein the different GUI configurations for different times are determined based on interaction between the current user and the GUI within a predetermined time range.

In Example 18, the subject matter of Examples 1-17 includes, wherein the learning engine includes a neural network.

In Example 19, the subject matter of Example 18 includes, wherein the neural network establishes a correlation between the at least one pattern of interaction with the current user, a history of interaction with the current user, and the configuration of the user model.

In Example 20, the subject matter of Example 19 includes, wherein a statistical model establishes the correlation between the at least one pattern of interaction with the current user, the history of interaction with the current user, and the configuration of the user model.

In Example 21, the subject matter of Examples 1-20 includes, wherein the validation comprises facial recognition.

In Example 22, the subject matter of Examples 1-21 includes, wherein the validation comprises fingerprint recognition.

In Example 23, the subject matter of Examples 1-22 includes, wherein the validation comprises password validation.

In Example 24, the subject matter of Examples 1-23 includes, wherein the validation comprises voice recognition.

In Example 25, the subject matter of Examples 1-24 includes, wherein the validation comprises multi-factor authentication.

In Example 26, the subject matter of Examples 1-25 includes, wherein the learning engine compares a current validation input and a prior validation input and, upon the current validation input being authenticated, automatically calibrates validation criteria with the current validation input.

In Example 27, the subject matter of Examples 1-26 includes, wherein the learning engine records the prior menu item usage of the current user in a log, wherein the log is used to generate the user-dependent configuration data.

In Example 28, the subject matter of Examples 1-27 includes, wherein an artificial intelligence engine analyzes the prior menu item usage of the automated sample analyzer by the current user to generate the user-dependent configuration data.

In Example 29, the subject matter of Examples 1-28 includes, wherein the at least one pattern of interaction is based, at least in part, on an amount of time the current user spent working at the automated sample analyzer.

In Example 30, the subject matter of Examples 1-29 includes, wherein the at least one pattern of interaction is based, at least in part, on a usage frequency of the automated sample analyzer by the current user.

In Example 31, the subject matter of Example 30 includes, wherein the usage frequency is indicated by color on the GUI.

In Example 32, the subject matter of Examples 1-31 includes, wherein the configuration control engine, provides, via the GUI, a representation of a most probable next action(s).

In Example 33, the subject matter of Examples 1-32 includes, wherein the configuration control engine, provides to the current user, via the GUI, a representation of a short-cut of sequential actions to an end action.

In Example 34, the subject matter of Examples 1-33 includes, wherein the configuration control engine, provides to the current user, via the GUI, a representation of a shortened workflow, the shortened workflow being selected based on an experience level of the current user identified by the learning engine.

In Example 35, the subject matter of Examples 1-34 includes, wherein the configuration control engine, provides, via the GUI, a representation of a shortened workflow, the shortened workflow being selected based on at least one previous menu item selection of the current user identified by the learning engine.

In Example 36, the subject matter of Examples 32-35 includes, wherein the representations are provided by playing audio via a speaker controlled by the user interface engine.

In Example 37, the subject matter of Examples 1-36 includes, wherein the artificial intelligence engine computes a user productivity value and correlates the user productivity value with at least one metric.

In Example 38, the subject matter of Example 37 includes, wherein the at least one metric includes uptime of the automated sample analyzer.

In Example 39, the subject matter of Examples 37-38 includes, wherein the at least one metric includes reliability of the automated sample analyzer.

In Example 40, the subject matter of Examples 1-39 includes, wherein the learning engine provides an output representing changes made to the user model and requests feedback, via the GUI, from the current user on the changes made to the user model.

In Example 41, the subject matter of Examples 1-40 includes, wherein the learning engine provides an output representing previous actions of the current user via the GUI.

In Example 42, the subject matter of Example 41 includes, wherein the output representing the previous actions is displayed in a pop-up window.

In Example 43, the subject matter of Examples 1-42 includes, wherein the learning engine generates an output representing previous actions that were previously presented in a menu that are not included in a corresponding set of current actions that were not previously presented in the menu.

In Example 44, the subject matter of Examples 1-43 includes, wherein the learning engine predicts a next action by image recognition.

In Example 45, the subject matter of Example 44 includes, wherein the learning engine provides an output instructing the current user how to operate hardware of the automated sample analyzer.

In Example 46, the subject matter of Example 45 includes, wherein the hardware of the automated sample analyzer includes a door for loading consumables.

In Example 47, the subject matter of Example 46 includes, wherein the learning engine shows the previous actions in a diagram displayed in the GUI, the GUI providing an interface for user selection of one or more of the previous actions for demonstration in the diagram.

In Example 48, the subject matter of Example 47 includes, wherein the user selection is done by clicking.

In Example 49, the subject matter of Examples 47-48 includes, the user selection selecting is done by touching.

In Example 50, the subject matter of Examples 47-49 includes, wherein the GUI changes a color of the current actions upon completion.

In Example 51, the subject matter of Examples 47-50 includes, wherein the current actions are color coded to indicate frequency.

In Example 52, the subject matter of Examples 1-51 includes, wherein the learning engine determines impairment of the current user.

In Example 53, the subject matter of Example 52 includes, wherein a report of impairment is transmitted by the learning engine if a predetermined level of impairment is detected.

In Example 54, the subject matter of Example 53 includes, wherein the report of impairment is transmitted to a supervisor of the current user.

Example 55 is a method comprising: receiving, at processing circuitry of an automated sample analyzer, measurements associated with a liquid sample placed into the automated sample analyzer from a sample analyzing device of the automated sample analyzer and storing the received measurements in a memory of the automated sample analyzer; setting, at the processing circuitry, a configuration of a user model to correspond to a current user of the automated sample analyzer; detecting and collecting, at the processing circuitry, at least one pattern of interaction of the current user with a graphical user interface (GUI); configuring, at the processing circuitry, the GUI according to user-dependent configuration data of the configuration of the user model corresponding to the current user, the user-dependent configuration data being received from a user data repository; and using a learning engine stored in the memory and executed by the processing circuitry: identifying an accessing user and, upon validation, establishing the accessing user as the current user; monitoring interaction between the current user and the GUI and storing interaction data of the current user in association with time; determining, based on the interaction data, at least one time-cyclical pattern of interaction between the current user and the GUI; and storing the at least one time-cyclical pattern of interaction.

Example 56 is a machine-readable medium storing instructions which, when executed by a machine, cause the machine to perform the method of Example 55.

Example 57 is an apparatus comprising means for performing the method of Example 55.

Example 58 is a method implemented at processing circuitry of an automated sample analyzer, the automated sample analyzer comprising the processing circuitry, a memory, a camera, and a sample input device, the method comprising: receiving, from the camera, image data representing a consumable for placement into the automated sample analyzer; classifying, using an image recognition engine stored in the memory, the consumable into a class of consumables based on the image data; transmitting, using the processing circuitry, a control signal to physically adjust the sample input device to receive the consumable, the control signal corresponding to the class of consumables.

In Example 59, the subject matter of Example 58 includes, transmitting, to a display device of the automated sample analyzer, a display signal for displaying a visual representation of the class of consumables or a portion of the image data.

In Example 60, the subject matter of Examples 58-59 includes, transmitting, to a display device of the automated sample analyzer, a display signal for displaying at least a portion of the image data.

In Example 61, the subject matter of Examples 58-60 includes, wherein physically adjusting the sample input device comprises providing access to a receptacle of the sample input device.

In Example 62, the subject matter of Example 61 includes, wherein providing access to the receptacle of the sample input device comprises opening a door.

Example 63 is an automated sample analyzer comprising: processing circuitry; a memory; a camera; and a sample input device, the memory storing instructions which, when executed by the processing circuitry, cause the processing circuitry to perform the method of any of Examples 58-62.

Example 64 is a machine-readable medium storing instructions which, when executed by a machine, cause the machine to perform the method of any of Examples 58-62.

Example 65 is an apparatus comprising means for performing the method of any of Examples 58-62.

Example 66 is at least one machine-readable medium including instructions that, when executed by processing circuitry, cause the processing circuitry to perform operations to implement of any of Examples 1-65.

Example 67 is an apparatus comprising means to implement of any of Examples 1-65.

Example 68 is a system to implement of any of Examples 1-65.

Example 69 is a method to implement of any of Examples 1-65.

Example 70 is a system comprising: processing circuitry; and a memory storing: a learning engine which, when executed by the processing circuitry, causes the processing circuitry to: identify an accessing user of an automated sample analyzer and, upon validation, establish the accessing user as a current user; monitor interactions between the current user and the automated sample analyzer to generate interaction data; determine, based on the interaction data, at least one pattern of interaction between the current user and the automated sample analyzer; determine, based on the at least one pattern of interaction, configuration data for the current user, the configuration data indicating at least one of an appearance of a graphical user interface displayed by the automated sample analyzer or a sequence of graphical user interfaces displayed by the automated sample analyzer; store the configuration data in a data repository in association with a user profile of the current user; a configuration control engine which, when executed by the processing circuitry, causes the processing circuitry to access the configuration data stored in the user data repository; and a user interface engine which, when executed by the processing circuitry, causes the processing circuitry to configure one or more graphical user interfaces for display by the automated sample analyzer according to the configuration data.

In Example 71, the subject matter of Example 70 includes, wherein the configuration control engine, when executed by the processing circuitry, causes the processing circuitry to: identify the accessing user and, upon validation, establish the accessing user as the current user; determine, based on a current time and the at least one pattern of interaction, a pattern of interaction for the current time; and cause display, within a graphical user interface of the automated sample analyzer, a shortcut to implement the pattern of interaction for the current time.

In Example 72, the subject matter of Example 70 or 71 includes, wherein the configuration control engine, when executed by the processing circuitry, causes the processing circuitry to: establish the accessing user as a new user, upon validation; and register the new user in the user data repository.

In Example 73, the subject matter of Examples 70-72 includes, wherein the configuration data includes menu optimization data that defines a menu optimization comprising a set of menus for presentation within one or more graphical user interfaces or a set of menu items for presentation within the menus of the one or more graphical user interfaces.

In Example 74, the subject matter of Example 73 includes, wherein the menu optimization data is derived from prior menu usage or prior menu item usage of the current user.

In Example 75, the subject matter of Example 74 includes, wherein the menu optimization data is derived by artificial intelligence menu usage review of the prior menu usage of the current user.

In Example 76, the subject matter of Example 75 includes, wherein an artificial intelligence engine analyzes a prior menu usage frequency of the current user to generate the configuration data.

In Example 77, the subject matter of Examples 75 or 76 includes, wherein the menu optimization is implemented without prompting the current user to cause the menu optimization.

In Example 78, the subject matter of Examples 70-77 includes, wherein the configuration data is updated in the user data repository and comprises different graphical user interface configurations for different times with at least a first graphical user interface configuration for a first time range and a second graphical user interface configuration for a second time range.

In Example 79, the subject matter of Example 78 includes, wherein the different graphical user interface configurations for different times are determined based on interaction between the current user and one or more graphical user interfaces displayed by the automated sample analyzer within a predetermined time range.

In Example 80, the subject matter of Examples 70-79 includes, wherein the learning engine includes a neural network.

In Example 81, the subject matter of Example 80 includes, wherein the neural network establishes a correlation between the at least one pattern of interaction with the current user, a history of interaction with the current user, and a configuration of the automated sample analyzer.

In Example 82, the subject matter of Examples 70-81 includes, wherein the learning engine records prior menu item usage of the current user in a log, and wherein the log is used to generate the configuration data.

In Example 83, the subject matter of Examples 70-82 includes, wherein an artificial intelligence engine analyzes prior menu item usage of the automated sample analyzer by the current user to generate the configuration data.

In Example 84, the subject matter of Examples 70-83 includes, wherein the at least one pattern of interaction is based, at least in part, on an amount of the current user spent working at the automated sample analyzer.

In Example 85, the subject matter of Examples 70-84 includes, wherein the at least one pattern of interaction is based, at least in part, on a usage frequency of the automated sample analyzer by the current user.

In Example 86, the subject matter of Examples 70-85 includes, wherein the configuration control engine, provides, via a graphical user interface, a representation of a most probable next action.

In Example 87, the subject matter of Examples 70-86 includes, wherein the configuration control engine, provides to the current user, via a graphical user interface, a representation of a short-cut of sequential actions to an action.

In Example 88, the subject matter of Examples 70-87 includes, wherein the configuration control engine, provides to the current user, via a graphical user interface, a representation of a shortened workflow, the shortened workflow being selected based on an experience level of the current user identified by the learning engine.

In Example 89, the subject matter of Examples 70-88 includes, wherein the configuration control engine, provides, via a graphical user interface, a representation of a shortened workflow, the shortened workflow being selected based on at least one previous menu item selection of the current user identified by the learning engine.

In Example 90, the subject matter of Examples 70-89 includes, wherein the learning engine provides an output representing changes made to the configuration data and requests feedback, via a graphical user interface, from the current user on the changes made to the configuration data.

In Example 91, the subject matter of Examples 70-90 includes, wherein the learning engine provides an output representing previous actions of the current user via a graphical user interface.

In Example 92, the subject matter of Example 91 includes, wherein the output representing the previous actions is displayed in a pop-up window.

In Example 93, the subject matter of Examples 70-92 includes, wherein the learning engine generates an output representing previous actions that were previously presented in a menu that are not included in a corresponding set of current actions that were not previously presented in the menu.

In Example 94, the subject matter of Examples 70-93 includes, wherein the learning engine predicts a next action by image recognition.

In Example 95, the subject matter of Example 94 includes, wherein the learning engine provides an output instructing the current user how to operate hardware of the automated sample analyzer.

In Example 96, the subject matter of Example 95 includes, wherein the hardware of the automated sample analyzer includes a door or an access panel for loading consumables.

In Example 97, the subject matter of Example 96 includes, wherein the learning engine shows the previous actions in a diagram displayed in a graphical user interface, the graphical user interface providing an interface for user selection of one or more of the previous actions for demonstration in the diagram.

Example 98 is a method comprising: identifying, by processing circuitry an accessing user of an automated sample analyzer and, upon validation, establish the accessing user as a current user; monitoring, by the processing circuitry, interactions between the current user and the automated sample analyzer to generate interaction data; determining, by the processing circuitry and based on the interaction data, at least one pattern of interaction between the current user and the automated sample analyzer; determining, by the processing circuitry and based on the at least one pattern of interaction, configuration data for the current user, the configuration data indicating at least one of an appearance of a graphical user interface displayed by the automated sample analyzer or a sequence of graphical user interfaces displayed by the automated sample analyzer; storing, by the processing circuitry, the configuration data in a user data repository in association with a user profile of the current user; accessing, by the processing circuitry, the configuration data stored in the user data repository; and configuring, by the processing circuitry, one or more graphical user interfaces for display by the automated sample analyzer according to the configuration data.

Example 99 is a method implemented at processing circuitry of an automated sample analyzer, the automated sample analyzer comprising the processing circuitry, a memory, a camera, and a sample input device, the method comprising: receiving, from the camera, image data representing a consumable for placement into the automated sample analyzer; classifying, using an image recognition engine stored in the memory, the consumable into a class of consumables based on the image data; transmitting, using the processing circuitry, a control signal to physically adjust the sample input device to receive the consumable, the control signal corresponding to the class of consumables.

In Example 100, the subject matter of Example 99, includes transmitting, to a display device of the automated sample analyzer, a display signal for displaying a visual representation of the class of consumables or a portion of the image data.

In Example 101, the subject matter of Examples 99 or 100 includes transmitting, to a display device of the automated sample analyzer, a display signal for displaying at least a portion of the image data.

In Example 102, the subject matter of Examples 99-101 includes, wherein physically adjusting the sample input device comprises providing access to a receptacle of the sample input device.

In Example 103, the subject matter of Example 102 includes, wherein providing access to the receptacle of the sample input device comprises opening a door or an access panel.

Although an implementation has been described with reference to specific example implementations, it will be evident that various modifications and changes may be made to these implementations without departing from the broader spirit and scope of the present disclosure. Accordingly, the specification and drawings are to be regarded in an illustrative rather than a restrictive sense. The accompanying drawings that form a part hereof show, by way of illustration, and not of limitation, specific implementations in which the subject matter may be practiced. The implementations illustrated are described in sufficient detail to enable those skilled in the art to practice the teachings disclosed herein. Other implementations may be utilized and derived therefrom, such that structural and logical substitutions and changes may be made without departing from the scope of this disclosure. This Detailed Description, therefore, is not to be taken in a limiting sense, and the scope of various implementations is defined only by the appended claims, along with the full range of equivalents to which such claims are entitled.

Although specific implementations have been illustrated and described herein, it should be appreciated that any arrangement calculated to achieve the same purpose may be substituted for the specific implementations shown. This disclosure is intended to cover any and all adaptations or variations of various implementations. Combinations of the above implementations, and other implementations not specifically described herein, will be apparent to those of skill in the art upon reviewing the above description.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, user equipment (UE), article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single implementation for the purpose of streamlining the disclosure. This method of disclosure is not to be interpreted as reflecting an intention that the claimed implementations require more features than are expressly recited in each claim. Rather, as the following claims reflect, inventive subject matter lies in less than all features of a single disclosed implementation. Thus the following claims are hereby incorporated into the Detailed Description, with each claim standing on its own as a separate implementation.

What is claimed is:

1. A system comprising:
processing circuitry; and
a memory storing:
a learning engine which, when executed by the processing circuitry, causes the processing circuitry to:
identify an accessing user of an automated sample analyzer and, upon validation, establish the accessing user as a current user;
monitor interactions between the current user and the automated sample analyzer to generate interaction data;
determine, based on interaction data, at least one pattern of interaction between the current user and the automated sample analyzer;
determine, based on the at least one pattern of interaction, configuration data for the current user, the configuration data indicating at least one of an appearance of a graphical user interface displayed by the automated sample analyzer or a sequence of graphical user interfaces displayed by the automated sample analyzer;
store the configuration data in a data repository in association with a user profile of the current user;
a configuration control engine which, when executed by the processing circuitry, causes the processing circuitry to access the configuration data stored by a user data repository; and
a user interface engine which, when executed by the processing circuitry, causes the processing circuitry to configure one or more graphical user interfaces for display by the automated sample analyzer according to the configuration data.

2. The system of claim 1, wherein the configuration control engine, when executed by the processing circuitry, causes the processing circuitry to:
identify the accessing user and, upon validation, establish the accessing user as the current user;
determine, based on a current time and the at least one pattern of interaction, a pattern of interaction for the current time; and
cause display, within a graphical user interface of the automated sample analyzer, a shortcut to implement the pattern of interaction for the current time.

3. The system of claim 1, wherein the configuration data includes menu optimization data that defines a menu optimization comprising a set of menus for presentation within one or more graphical user interfaces or a set of menu items for presentation within the set of menus of the one or more graphical user interfaces.

4. The system of claim 3, wherein the menu optimization data is derived by artificial intelligence menu usage review of prior menu usage of the current user.

5. The system of claim 4, wherein an artificial intelligence engine analyzes a prior menu usage frequency of the current user to generate the configuration data.

6. The system of claim 1, wherein the configuration data is updated in the user data repository and comprises different graphical user interface configurations for different times with at least a first graphical user interface configuration for a first time range and a second graphical user interface configuration for a second time range.

7. The system of claim 6, wherein the different graphical user interface configurations for different times are determined based on interaction between the current user and one or more graphical user interfaces displayed by the automated sample analyzer within a predetermined time range.

8. The system of claim 1, wherein the learning engine includes an artificial neural network and the artificial neural network establishes a correlation between the at least one pattern of interaction with the current user, a history of interaction with the current user, and a configuration of the automated sample analyzer.

9. The system of claim 1, wherein the learning engine predicts a next action by image recognition.

10. The system of claim 1, wherein the learning engine shows previous actions of the current user in a diagram displayed in a graphical user interface, the graphical user interface providing an interface for user selection of one or more of the previous actions for demonstration in the diagram.

11. A method comprising:
identifying, by processing circuitry, an accessing user of an automated sample analyzer and, upon validation, establish the accessing user as a current user;
monitoring, by the processing circuitry, interactions between the current user and the automated sample analyzer to generate interaction data;
determining, by the processing circuitry and based on the interaction data, at least one pattern of interaction between the current user and the automated sample analyzer;
determining, by the processing circuitry and based on the at least one pattern of interaction, configuration data for the current user, the configuration data indicating at least one of an appearance of a graphical user interface displayed by the automated sample analyzer or a sequence of graphical user interfaces displayed by the automated sample analyzer;
storing, by the processing circuitry, the configuration data in a user data repository in association with a user profile of the current user;
accessing, by the processing circuitry, the configuration data stored in the user data repository; and
configuring, by the processing circuitry, one or more graphical user interfaces for display by the automated sample analyzer according to the configuration data.

12. The method of claim 11 comprising:
receiving, from a camera of the automated sample analyzer, image data representing a consumable for placement into the automated sample analyzer;
classifying, using the processing circuitry, the consumable into a class of consumables based on the image data; and
transmitting, using the processing circuitry, a control signal to physically adjust a sample input device of the automated sample analyzer to receive the consumable, the control signal corresponding to the class of consumables.

13. The method of claim 12, further comprising:
transmitting, to a display device of the automated sample analyzer, a display signal for displaying a visual representation of the class of consumables or a portion of the image data.

14. An automated sample analyzer comprising:
a sample input device receiving a liquid sample;
a sample analyzing device reading measurements associated with the liquid sample;
a display device displaying a graphical user interface (GUI) to a current user of the automated sample analyzer, the GUI being for controlling or maintaining the automated sample analyzer by the current user;

processing circuitry; and a memory storing:

a receiving engine which, when executed by the processing circuitry, receives the measurements associated with the liquid sample from the sample analyzing device and stores the measurements in memory;

a configuration control engine which, when executed by the processing circuitry, causes the processing circuitry to set a configuration of a user model to correspond to the current user of the automated sample analyzer;

a learning engine which, when executed by the processing circuitry, causes the processing circuitry to detect and collect at least one pattern of interaction of the current user with the GUI; and a user interface engine which, when executed by the processing circuitry, causes the processing circuitry to configure the GUI according to user-dependent configuration data of the configuration of the user model corresponding to the current user, the user-dependent configuration data being received from a user data repository;

wherein the learning engine, when executed by the processing circuitry, causes the processing circuitry to:

identify an accessing user and, upon validation, establish the accessing user as the current user;

monitor interaction between the current user and the GUI and store interaction data of the current user in association with time;

determine, based on the interaction data, at least one time-cyclical pattern of interaction between the current user and the GUI; and store the at least one time-cyclical pattern of interaction.

15. The automated sample analyzer of claim 14, wherein the user-dependent configuration data includes menu optimization data that defines a menu optimization comprising a set of menus for presentation within the GUI or a set of menu items for presentation within the set of menus of the GUI; and the user interface engine, when executed by the processing circuitry; causes the processing circuitry to:

display an optimized version of a menu;

receive, via the GUI, a request to revert to a prior version of the menu; and responsive to the request, display the prior version of the menu.

16. The automated sample analyzer of claim 14, wherein the learning engine compares a current validation input and a prior validation input and, upon the current validation input being authenticated, automatically calibrates validation criteria with the current validation input.

17. The automated sample analyzer of claim 14, wherein the configuration control engine, provides to the current user, via the GUI, a representation of a short-cut of sequential actions to an end action.

18. The automated sample analyzer of claim 14, wherein the configuration control engine, provides to the current user, via the GUI, a representation of a shortened workflow, the shortened workflow being selected based on an experience level of the current user identified by the learning engine.

19. The automated sample analyzer of claim 14, wherein the configuration control engine, provides, via the GUI, a representation of a shortened workflow, the shortened workflow being selected based on at least one previous menu item selection of the current user identified by the learning engine.

20. The automated sample analyzer of claim 14, wherein the learning engine provides an output representing changes made to the user model and requests feedback, via the GUI, from the current user on the changes made to the user model.

*    *    *    *    *